United States Patent
Gorr

(10) Patent No.: US 8,569,449 B2
(45) Date of Patent: Oct. 29, 2013

(54) SYNTHETIC PEPTIDES AND PEPTIDE MIMETICS

(75) Inventor: Sven-Ulrik Gorr, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 853 days.

(21) Appl. No.: 12/599,021

(22) PCT Filed: May 8, 2008

(86) PCT No.: PCT/US2008/063098
§ 371 (c)(1),
(2), (4) Date: Dec. 10, 2009

(87) PCT Pub. No.: WO2008/138001
PCT Pub. Date: Nov. 13, 2008

(65) Prior Publication Data
US 2012/0058933 A1    Mar. 8, 2012

Related U.S. Application Data

(60) Provisional application No. 60/916,621, filed on May 8, 2007, provisional application No. 61/023,120, filed on Jan. 24, 2008.

(51) Int. Cl.
*C07K 7/08* (2006.01)
(52) U.S. Cl.
USPC .................. 530/327; 530/324; 530/326
(58) Field of Classification Search
None
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,612,302 A | 9/1986 | Szabo et al. |
| 4,684,620 A | 8/1987 | Hryby et al. |
| 4,820,508 A | 4/1989 | Wortzman |
| 4,853,371 A | 8/1989 | Coy et al. |
| 4,938,949 A | 7/1990 | Borch et al. |
| 4,992,478 A | 2/1991 | Geria |
| 2004/0202670 A1 | 10/2004 | Apicella |
| 2004/0224357 A1 | 11/2004 | Duan et al. |
| 2009/0110756 A1 | 4/2009 | McCray, Jr. et al. |

FOREIGN PATENT DOCUMENTS

| | | | |
|---|---|---|---|
| WO | WO 98/21329 A1 | | 5/1998 |
| WO | WO 0157275 | * | 8/2001 |

OTHER PUBLICATIONS

Rudinger. In Peptide Hormones. Editor J.A. Parsons. Copyright Jun. 1976.*
Geetha et al., "Expression and anti-bacterial activity of human parotid secretory protein (PSP)", *Biochemical Society Transactions 31*(Pt.4), 815-818 (2003).
Geetha et al., "Design and Validation of Anti-inflammatory Peptides from Human Parotid Secretory Protein", *J Dent Res*, vol. 84, No. 2, 149-153 (2005).
Norris et al., "Ultrasonically Controlled Release of Ciprofloxacin from Self-Assembled Coatings on Poly(2-Hydroxyethyl Methacrylate) Hydrogels for *Pseudomonas aeruginosa* Biofilm Prevention", *Antimicrob. Agents Chemother*, 49, 4272-4279 (2005).
Patent Cooperation Treaty, International Search Report and Written Opinion for PCT Application No. PCT/US2008/063098, 13 pages, Oct. 27, 2008.
Rasmussen et al., "Quorum sensing inhibitors, a bargain of effects", *Microbiology*, 152, 895-904 (2006).
Robinson et al., "PSP expression in murine lacrimal glands and function as a bacteria binding protein in exocrine secretions", *Am J Physiol 272*(4 Pt 1), G863-871 (1997).
Shiba et al., "Parotid Secretory Protein is Expressed and Inducible in Human Gingival Keratinocytes", *Journal of Periodontal Research*, vol. 40, No. 2, 153-157 *Abstract* (2005).
Weijmer et al., "Randomized, Clinical Trial Comparison of Trisodium Citrate 30% and Heparin as Catheter-Locking Solution in Hemodialysis Patients 10.1681/ASN.2004100870" *J. Am Soc Nephrol*, 16, 2769-2777 (2005).
Bingle et al., "Host defense in oral and airway epithelia: chromosome 20 contributes a new protein family", *The International Journal of Biochemistry and Cell Biology*, vol. 36, No. 11, 2144-2152 (2004).

* cited by examiner

*Primary Examiner* — Robert C Hayes
*Assistant Examiner* — Lori K Mattison
(74) *Attorney, Agent, or Firm* — Viksnins Harris & Padys PLLP

(57) ABSTRACT

The present invention provides Parotid Secretory Protein peptides, nucleic acids encoding the peptides, and methods of using the peptides, and methods of screening GL13 mimetics.

6 Claims, 24 Drawing Sheets

FIG. 1

SEQUENCE OF HUMAN PSP

```
1    MLQLWKLVLL CGVLTGTSES LLDNLGNDLS NVVDKLEPVL HEGLETVDNT LKGILEKLKV
61   DLGVLQKSSA WQLAKQKAQE AEKLLNNVIS KLLPTNTDIF GLKISNSLIL DVKAEPIDDG
121  KGLNLSFPVT ANVTVAGPII GQIINLKASL DLLTAVTIET DPQTHQPVAV LGECASDPTS
181  ISLSLLDKHS QIINKFVNSV INTLKSTVSS LLQKEICPLI RIFIHSLDVN VIQQVVDNPQ
241  HKTQLQTLI
```

Fig. 2C
Fig. 2D
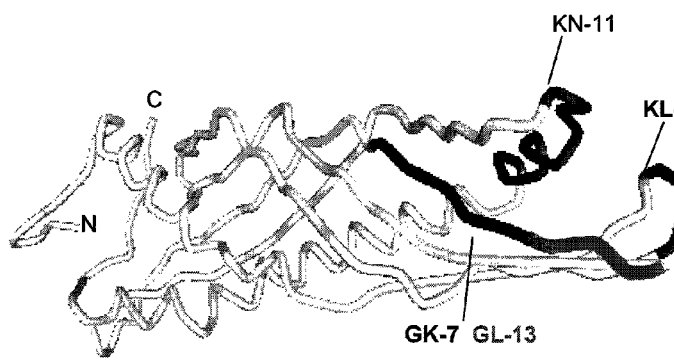
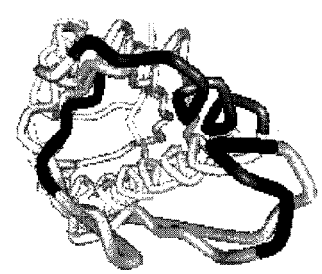
End view

No peptide

Lysozyme

GL-13

SYNTHETIC PEPTIDES AND PEPTIDE MIMETICS

PRIORITY OF INVENTION

This application is related to and claims priority under 35 U.S.C. §119(e) to U.S. Provisional Application No. 60/916,621 filed on May 8, 2007 and to U.S. Provisional Application No. 61/023,120 filed on Jan. 24, 2008, which are incorporated herein by reference.

BACKGROUND OF THE INVENTION

The oral cavity and upper airways are major entry points for bacteria and other microorganisms. The oral cavity hosts over 700 species of bacteria that do not cause disease in otherwise healthy individuals. In immunocompromised individuals, however, otherwise harmless bacteria can cause serious infections. As an example, *Pseudomonas aeruginosa* is an environmental bacterium that does not typically cause disease in healthy individuals. It is, however, the leading cause of death in cystic fibrosis patients, causes nocosomial infections that are fatal in up to 50% of cases, and causes serious infections in other immunocompromised patients, including cancer and burn patients. *Aggregatibacter* (*Actinobacillus*) *actinomycetemcomitans* is an oral Gram-negative coccobacillus that is associated with periodontal disease, in particular Localized Aggressive Periodontitis, but is also found in healthy individuals. The factors that allow these opportunistic pathogens to cause disease in some, but not all, infected individuals are poorly understood but it is likely that deficiencies in both innate and acquired immunity are behind increased susceptibility to these bacteria.

Biofilms are a significant problem in health care in public health areas. Bacteria in biofilms are very difficult to eradicate and cause substantial mortality due to resistance to antibiotics. Medical device that enter the body are typical areas for bacterial biofilm formation.

Currently, there is a need for compositions and methods of treating infections associated with biofilm-producing bacteria, and for preventing the attachment of bacteria to medical devices.

SUMMARY OF THE INVENTION

The present inventors have designed several peptides based on the sequences of human Parotid Secretory Protein (PSP, also called SPLUNC2 or C20ORF70).

TABLE 1

PSP peptides

| Peptide | Sequence | SEQ ID NO: | pI | Net Charge |
|---|---|---|---|---|
| GK7 | GQIINLK | SEQ ID NO: 1 | 10.1 | +1 |
| KN11 | KAQEAEKLLNN | SEQ ID NO: 2 | 7.1 | 0 |
| KL11 | KLLNNVISKLL | SEQ ID NO: 3 | 10.6 | +2 |
| KK9 | KLLNNVISK | SEQ ID NO: 4 | 10.6 | +2 |
| GL13-OH | GQIINLKASLDLL | SEQ ID NO: 5 | 6.7 | 0 |
| GL13-NH₂ (also called GL13) | GQIINLKASLDLL-(CONH₂) | SEQ ID NO: 7 | 10.1 | +1 |
| GL13-D/N-NH2 | GQIINLKASLNLL-(CONH₂) | SEQ ID NO: 8 | 14 | +2 |
| GL13-D/N | GQIINLKASLNLL-(COOH) | SEQ ID NO: 9 | 10.1 | +1 |
| GL13-Q/N | GQIINLKASLQLL | SEQ ID NO: 11 | 10.1 | +1 |
| GL13-K/N | GQIINLKASLKLL | SEQ ID NO: 12 | 10.6 | +2 |
| GL13-R/N | GQIINLKASLRLL | SEQ ID NO: 13 | 11.5 | +2 |

PSP expression is regulated by bacteria and the cytokine TNFα. PSP binds lipopolysaccharide (LPS). The peptide GL-13 inhibits LPS action on macrophages, and activity is better than that of polymyxin B. LPS binding does not depend on glycosylation. PSP peptides have bactericidal activity against *P. aeruginosa*, 90% killing in no more than two hours. Little activity was observed against *A. actinomycetemcomitans*, which suggests that the peptides may be selective for some pathogens. It was observed that PSP peptides were not bacteriostatic against *P. aeruginosa* and *A. actinomycetemcomitans*. It was observed that PSP peptides inhibit biofilm formation but do not eliminate established biofilm. The PSP peptides prevented infection in the lettuce leaf infection model.

GL13 appears to block the invasion of epithelial cell monolayers by *P. aeruginosa*. PSP peptides do not appear to block the production of bacterial virulence factors. GL-13 causes agglutination of *P. aeruginosa*, *A. actinomycetemcomitans* and *S. gordonii*. Agglutination is an established antibacterial activity in saliva (e.g., GP340). PSP peptides do not induce an inflammatory response in macrophages and do not appear to cause cell death in mammalian cells.

The present invention provides an isolated and purified Parotid Secretory Protein (PSP) peptide of seven to 50 amino acids in length that is GK7, KN11, KL11, KK9 or GL13.

The present invention further provides an isolated and purified Parotid Secretory Protein (PSP) peptide of seven to 50 amino acids in length comprising GK7, KN11, KL11, KK9 or GL13, which is amidated at its C-terminal end.

In certain embodiments, the peptide of the present invention is between seven and 20 amino acids in length; between seven and 15 amino acids in length; or between seven and 13 amino acids in length. In certain embodiments, the peptide of the present invention is amidated at its C-terminal end. In one embodiment the peptide is GL13, and the peptide has been amidated at its C-terminal end. In one embodiment, the peptide has an Asn for Asp substitution (GL13-D/N or GL13-D/N—NH2). In other embodiments, Asp is replaced by Gln, Lys or Arg.

In certain embodiments, the peptide of the present invention the peptide is circular or linear.

The present invention also provides a therapeutic method for preventing or treating a pathological condition or symptom in a mammal, such as a human, wherein an antibiotic activity is implicated and antagonism of its action is desired, comprising administering to a mammal in need of such therapy, an effective amount of PSP peptide GK7, KN11, KL11, KK9 or GL13.

The present invention also provides a therapeutic method for preventing or treating a pathological condition or symptom in a mammal, such as a human, wherein an anti-inflammatory activity is implicated and antagonism of its action is desired, comprising administering to a mammal in need of such therapy, an effective amount of PSP peptide GK7, KN11, KL11, KK9 or GL13.

A therapeutic method for preventing or treating a pathological condition or symptom in a mammal, such as a human, wherein sepsis is implicated and antagonism of its action is desired, comprising administering to a mammal in need of such therapy, an effective amount of PSP peptide GK7, KN11, KL11, KK9 or GL13.

A therapeutic method for preventing or treating a pathological condition or symptom in a mammal, such as a human, wherein peritonitis is implicated and antagonism of its action is desired, comprising administering to a mammal in need of such therapy, an effective amount of PSP peptide GK7, KN11, KL11, KK9 or GL13.

The present invention also provides a method to treat a microbial infection comprising of administering a therapeutically effective amount of a PSP peptide GK7, KN11, KL11, KK9 or GL13 to a mammal. The present invention also provides a method of inducing bacterial agglutination comprising contacting bacteria with a PSP peptide GK7, KN11, KL11, KK9 or GL13. In certain embodiments, the microbes are gram-negative bacteria. In certain embodiments, the bacteria are *Pseudomonas aeruginosa* or *Aggregatibacter (Actinobacillus) actinomycetemcomitans* In certain embodiments, the peptide is KL11 and the bacteria are *Aggregatibacter (Actinobacillus) actinomycetemcomitans*. In certain embodiments, the peptide is GL13 and the bacteria are *Pseudomonas aeruginosa*. In certain embodiments, the microbes are gram-positive bacteria. In certain embodiments, the bacteria are *Streptococcus gordonii*. In certain embodiments, the peptide is GL13 and the bacteria are *Streptococcus gordonii*.

The present invention provides a compound that includes a PSP peptide GK7, KN11, KL11, KK9 or GL 13 for use in medical therapy.

The present invention provides a use of a compound that includes a PSP peptide GK7, KN11, KL11, KK9 or GL13 for the manufacture of a medicament useful for the treatment of a microbial infection in a mammal.

The present invention provides a method of preventing the adhesion of bacteria on a solid substrate comprising contacting the solid substrate with a peptide GK7, KN11, KL11, KK9 or GL13.

The present invention provides a method of preventing the formation of biofilm of bacteria in vivo by contacting a tissues surface with a peptide GK7, KN11, KL11, KK9 or GL13. In certain embodiments, the tissue is tissue in the respiratory system, such as oral or lung tissue, or a mucosal surface.

The present invention provides a method of preventing the formation of a biofilm of bacteria on a solid substrate comprising contacting the solid substrate with a peptide a peptide GK7, KN11, KL11, KK9 or GL13. In certain embodiments, the solid substrate is a medical device. In certain embodiments, the medical device is a ventilator tube or a catheter. In certain embodiments, the solid substrate is a polypropylene or PVC surface. In certain embodiments, the bacteria are gram-negative bacteria, such as *Pseudomonas aeruginosa* or *Aggregatibacter (Actinobacillus) actinomycetemcomitans*. In certain embodiments, the peptide is KL11 and the bacteria are *Aggregatibacter (Actinobacillus) actinomycetemcomitans*. In certain embodiments, the peptide is GL13 and the bacteria are *Pseudomonas aeruginosa*.

The present invention provides an isolated or purified nucleic acid that is less than 150 nucleotides in length encoding a peptide GK7, KN11, KL11, KK9 or GL13. In certain embodiments, the isolated or purified nucleic acid encodes peptide KL11 or GL13.

The present invention provides an expression cassette including a nucleic acid that is less than 150 nucleotides in length encoding a peptide GK7, KN11, KL11, KK9 or GL13. In certain embodiments, the expression cassette further includes a promoter. In certain embodiments, the expression cassette further includes a marker gene. In certain embodiments the marker gene is fused in frame to the PSP peptide sequence so as to produce a fusion protein containing the PSP peptide sequence. In certain embodiments the expression cassette further comprises a cleavable sequence that allows the specific release of the PSP peptide form the fusion protein.

The present invention provides a vector that contains the expression cassette including a nucleic acid that is less than 150 nucleotides in length encoding a peptide GK7, KN11, KL11, KK9 or GL13.

The present invention provides a cell that contains expression cassette including a nucleic acid that is less than 150 nucleotides in length encoding a peptide GK7, KN11, KL11, KK9 or GL13.

The peptide could be administered as a prophylactic during procedures that are known to carry a high risk of infection and biofilm formation. The present biofilm inhibitors are based on a human protein and the initial data support the expectation that they have low toxicity, unlike currently-known biofilm inhibitors (e.g., patulin and PA).

A composition comprising the a peptide GK7, KN11, KL11, KK9 or GL13, and a pharmaceutically acceptable carrier.

A dental hygiene product comprising the peptide of claim 1 or 2, and an acceptable carrier. Dental hygiene products are well known in the art, and include, for example, toothpaste, mouthwash, and dental floss.

A method of screening GL 13 mimetic comprising antimicrobial and anti-inflammatory assays, including competition assays with dansylated peptides.

BRIEF DESCRIPTION OF THE FIGURES

FIG. 1: Amino-acid sequence of human PSP (SEQ ID NO:6). The sequences of KL11 (bold), GK7 (bold, underlined) and GL13 (underlined) are indicated. The signal peptide is in italics.

Figure 4:
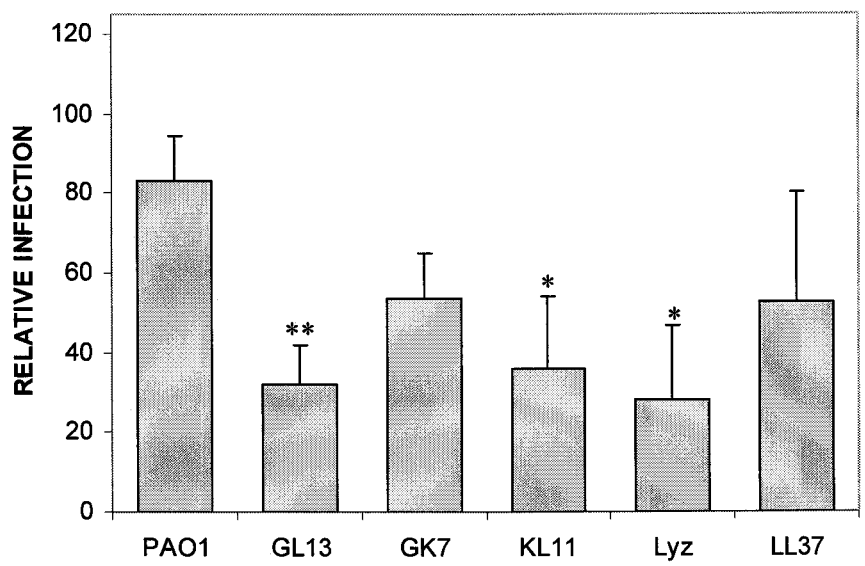

FIG. 4: Antibacterial activity in vivo. Romaine lettuce leaves were injected with *P. aeruginosa* ($10^8$ cells/ml) in the presence or absence of 200 μg/ml of antibacterial peptides. After 2-3 days incubation the injection sites were scored for infection on a scale of 0-100% relative to the no-bacteria (0% infection) and bacteria-only controls (PAO1) (100%). Data are from six independent experiments and are shown as mean±SEM, N=4-12. *) P<0.04, **) P<0.003. GL13 and KL11 significantly inhibit *P. aeruginosa* infection in the Romaine lettuce model.

Figure 5A:
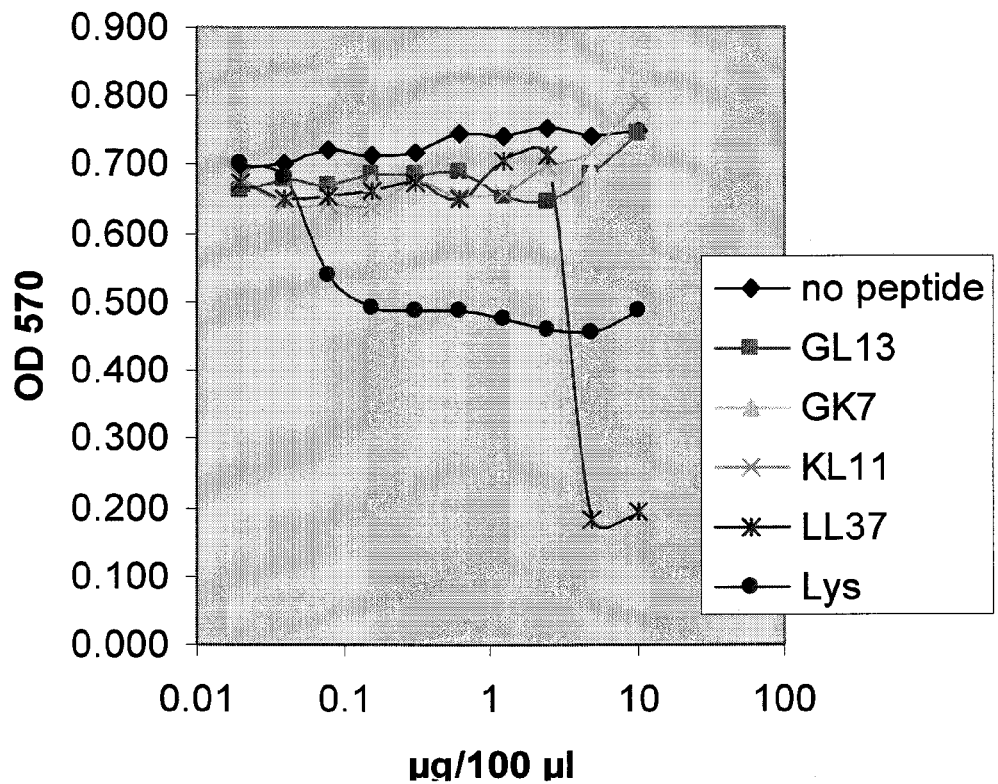
Figure 5B:
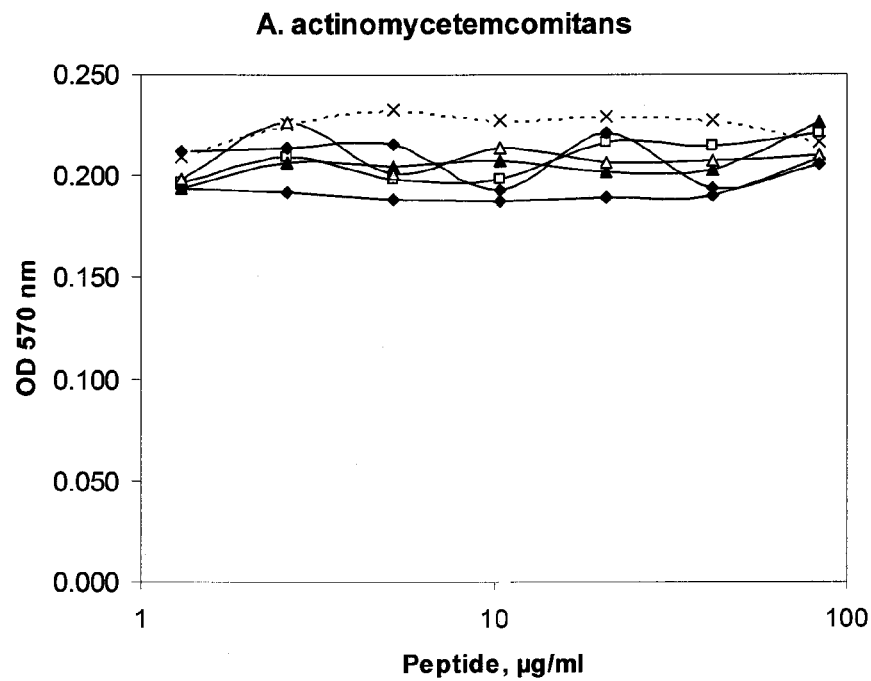

FIGS. 5A and 5B: PSP peptides lack bacteriostatic activity. *P. aeruginosa* PAO1 or *A. actinomycetemcomitans* JP2 ($10^5$ cells/ml) were incubated overnight with two-fold serial dilutions of the indicated peptides. The OD was determined at 570 nm. The data for *P. aeruginosa* (FIG. 5A) are representative of six independent experiments. The data for *A. actinomycetemcomitans* (FIG. 5B) are representative of three independent experiments. Filled squares, lysozyme; open diamonds, no peptide; open triangles, KL-11; filled triangles, GK-7; open squares, GL-13; filled diamonds, LL-37. The MIC for LL37 against *P. aeruginosa* is 42 μg/ml. Lysozyme inhibits growth about 50%. None of the PSP peptides inhibit growth.

Figure 6A:
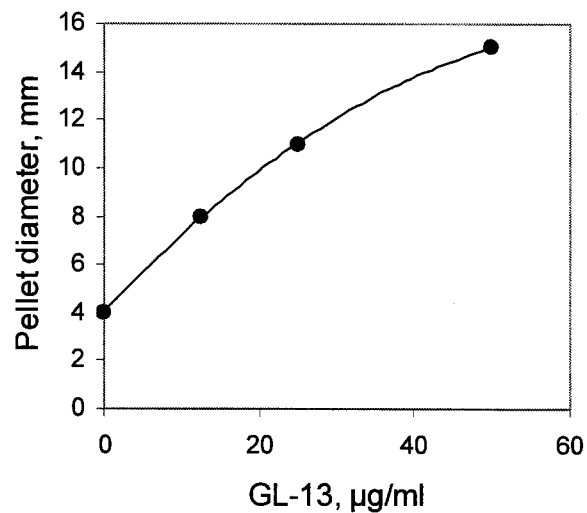
Figure 6B:
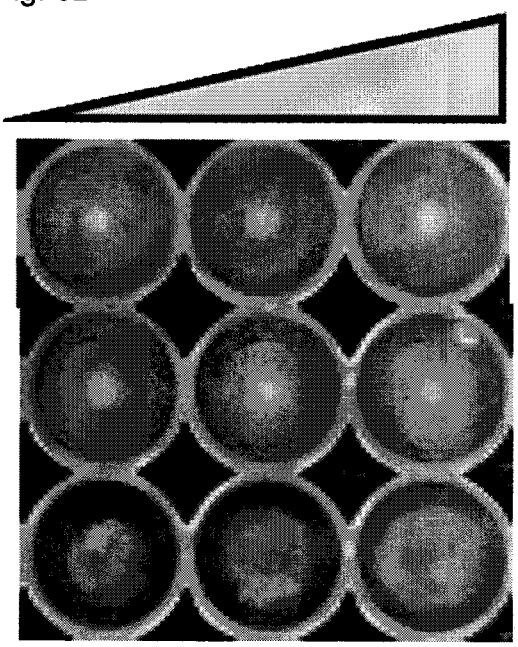
Figure 6C:
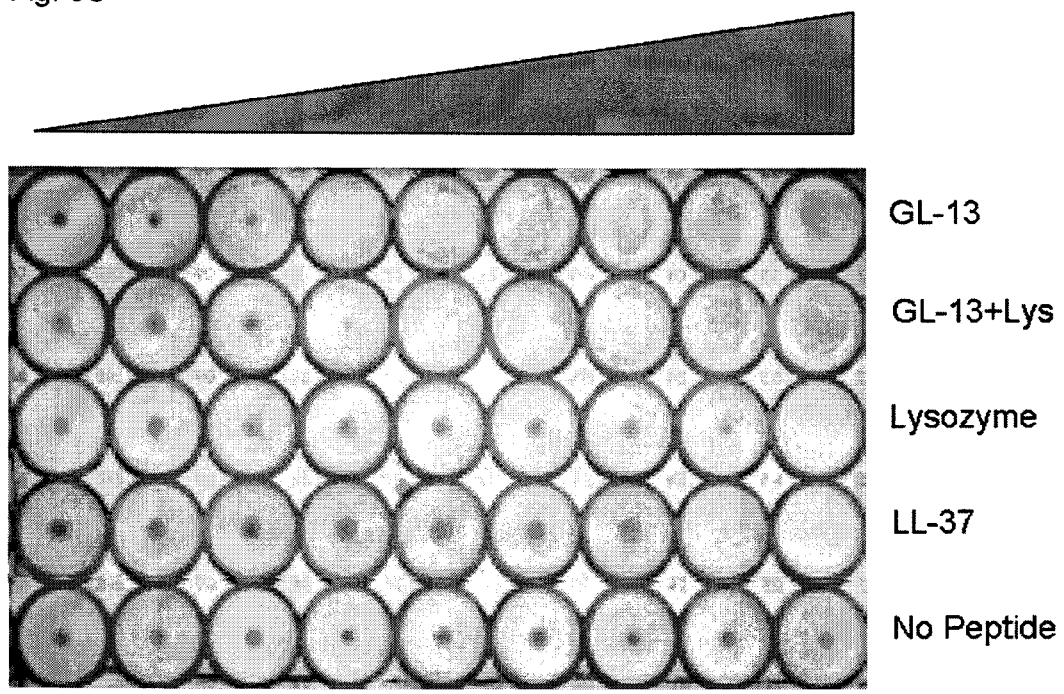

FIG. 6A-6C: GL13 causes bacterial cell spreading. Microtiter plates used to determine bacteriostatic activity (FIG. 5) were photographed after overnight incubation with serial dilutions of the indicated peptides. The diameter of the *P. aeruginosa* pellets in the presence of GL13 was determined and expressed relative to the peptide concentration in each well. A. Graph of the results. B and C are representative depictions of *P. aeruginosa* and *A. actinomycetemcomitans*, respectively, spreading in the presence of PSP peptides.

Figure 7:
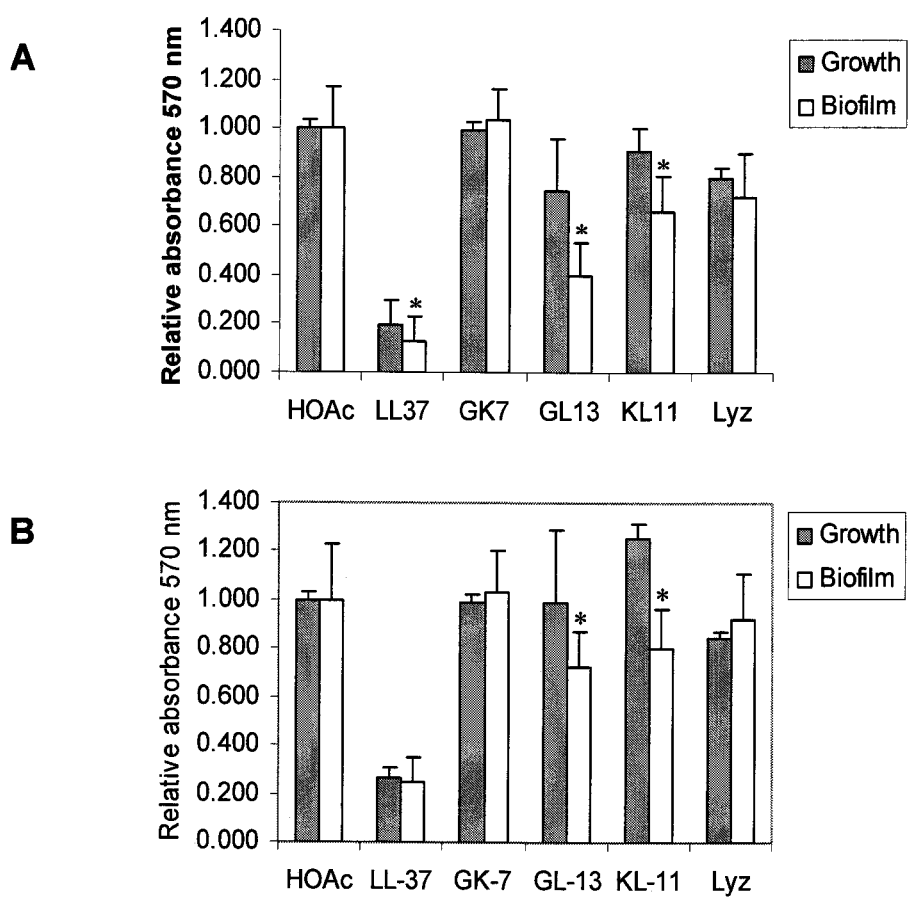

FIGS. 7A and 7B: PSP-peptides inhibit biofilm formation. *P. aeruginosa* PAO1 (overnight cultures, diluted 1:100 were incubated with 50 μg/ml of each peptide (LL37, GK7, GL13, KL11) or lysozyme for 6 h under aerobic (FIG. 7A) or reduced oxygen (anaerobic) (FIG. 7B) conditions. The OD 570 (growth) was determined and the attached cells were then quantitated by staining with crystal violet (biofilm). Growth and biofilm values were normalized against the mean of samples without peptides (HOAc) and expressed as mean±SEM. The data in panel A are from three independent experiments, N=22-24. The data in panel B are from two independent experiments, N=16. Lysozyme (Lyz) data are from a single experiment, N=8. *) different from Growth, P<0.002

Figure 8:
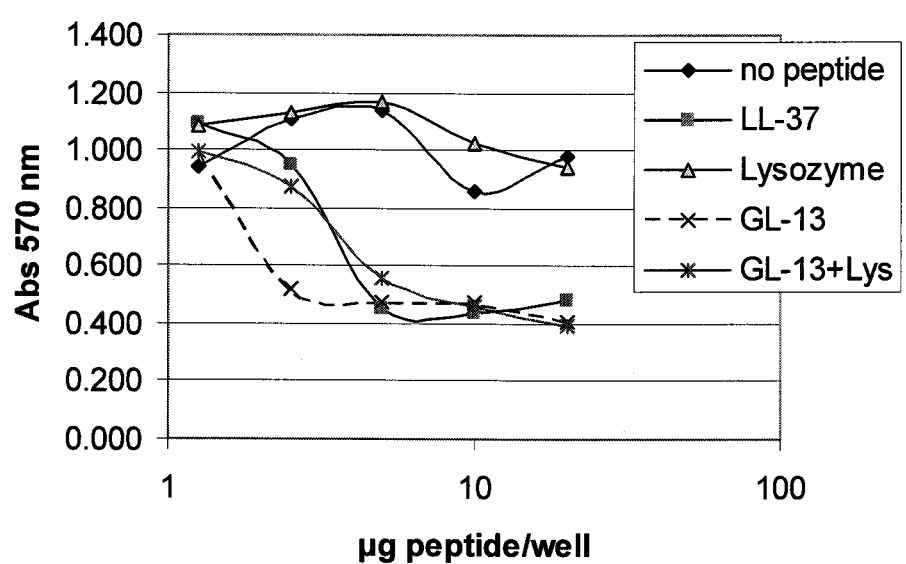

FIG. 8. Inhibition of *A. actinomycetemcomitans* biofilm formation. An overnight culture of *A. actinomycetemcomitans* JP2 in Mueller-Hinton broth was diluted to $10^5$ cells/ml and incubated in microtiter plate with two-fold serial dilutions of PSP or control peptides. Incubated at 35° C. for 48 h under reduced oxygen conditions. The plate was washed in PBS and stained with Coommassie blue. The wells were rinsed with water and the bound dye dissolved in 95% ethanol and quantitated at 570 nm.

Figure 9:
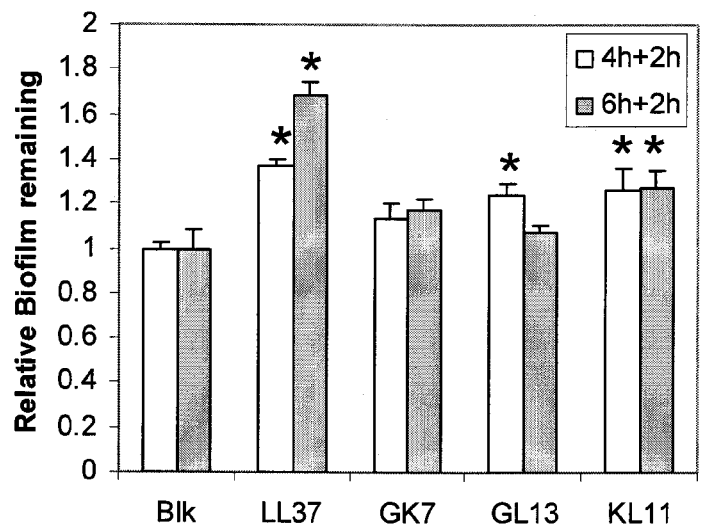

FIG. 9: Elimination of bacterial biofilm. PVC microtiter plates were incubated with *P. aeruginosa* for 4 h (open bars) or 6 h (shaded bars) followed by incubation with peptides for 2 h. Attached cells (remaining biofilm) were stained with crystal violet and quantitated spectrophotometrically at 570 nm. The data were normalized to the mean of the control samples (Blk), *) different from Blk, P<0.05, N=8.

Figure 10:
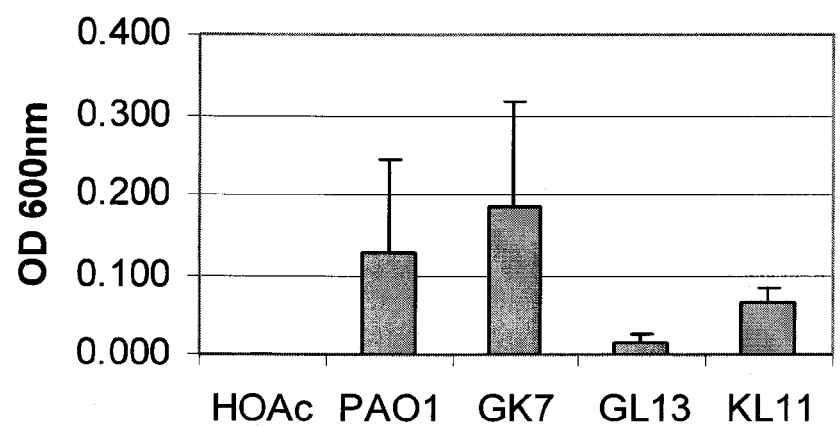

FIG. 10. MDCK monolayer penetration: MDCK cells were cultured on filter supports and infected on the apical side with $10^6$ CFU/ml of *P. aeruginosa* PAO1 (PAO1) or bacteria mixed with PSP peptides, as indicated. Control MDCK cells were incubated with buffer alone (HOAc). After 24 h incubation at 37° C., the OD 600 nm was determined for the media in the basolateral compartment to detect bacterial penetration of the MDCK cell monolayer.

Figure 11:
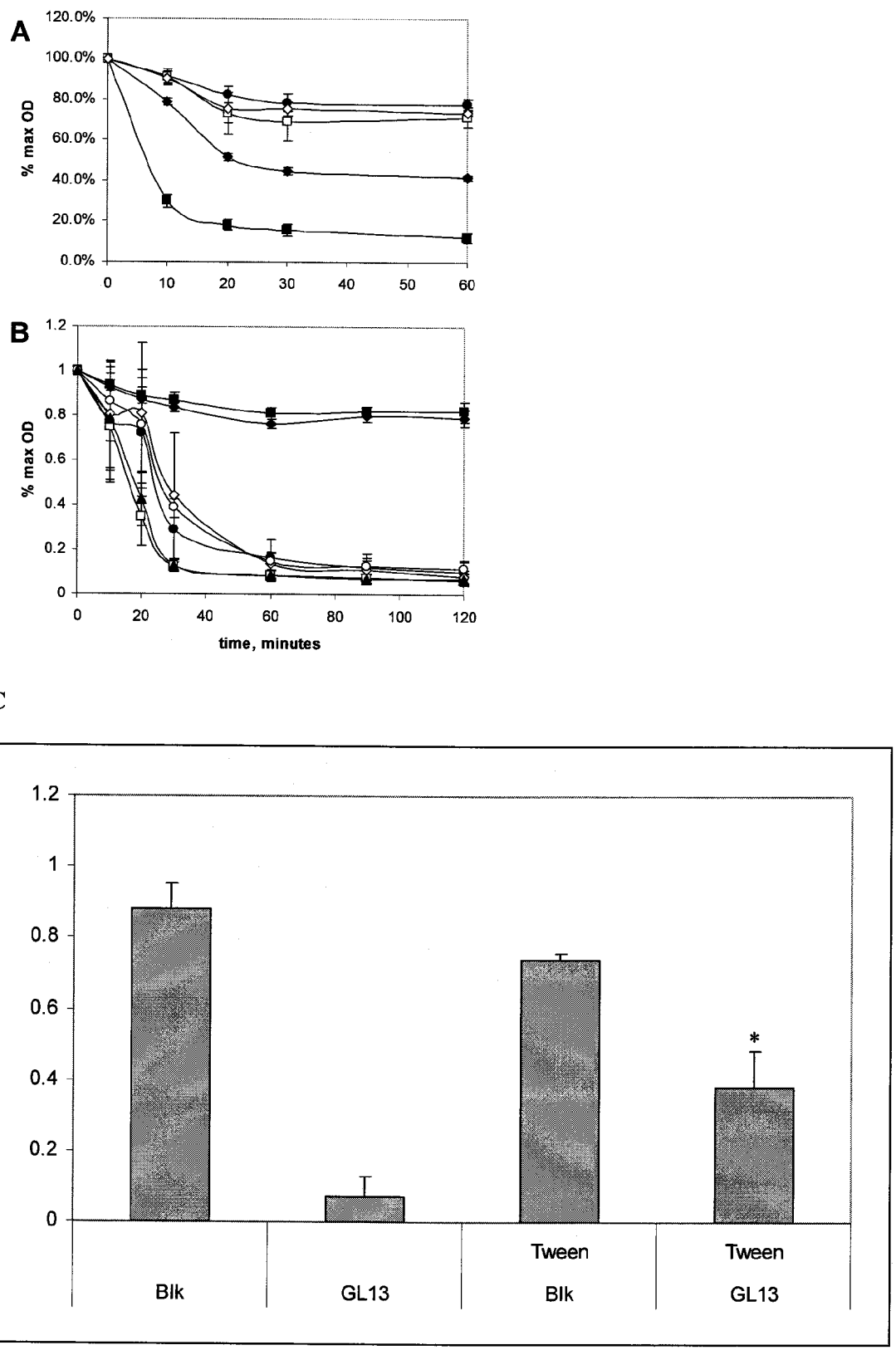

FIG. 11: Time-course of *P. aeruginosa* agglutination. FIG. 11A. *P. aeruginosa* (OD 675 nm 0.6) was incubated with serial dilutions of GL-13-NH2 for 60 min at room temperature: Filled squares: 100 μg/ml; filled diamonds: 50 μg/ml; filled circles: 25 μg/ml; open squares: 12.5 μg/ml; open diamonds: 6.25 μg/ml. The OD 675 nm was recorded at the times indicated. The data from three independent experiments were expressed as a percentage of starting OD and are shown as mean±SEM (N=3). FIG. 11B. *P. aeruginosa* (OD 675 nm 0.6) were incubated with buffer (HOAc) (filled squares), GK-7 (100 μg/ml) (filled diamonds), GL-13-NH2 (100 μg/ml) alone (filled circles) or GL-13-NH2 with salt additions: 70 μM EDTA (open squares), 1 mM $CaCl_2$ (open diamonds), 250 nm NaCl (open circles) or 250 nM glucose (filled triangles). The OD 675 nm was recorded at the times indicated. The data from three independent experiments were expressed as a percentage of starting OD and are shown as mean±SEM (N=3). Agglutination is complete after 30 minutes and does not depend on divalent cations. FIG. 11C: GL-13-NH2 induced agglutination is partially inhibited by the non-ionic detergent Tween-20, suggesting that agglutination depends partially on hydrophobic interactions. *P. aeruginosa* PAO1 were incubated with or without GL-13-NH2 (100 μg/ml) and Tween-20 (0.25%). The optical density at 675 nm was recorded after 2 h incubation. Data are expressed as mean±SEM. *) different from GL-13-NH2 alone, P<0.012.

Figure 12:
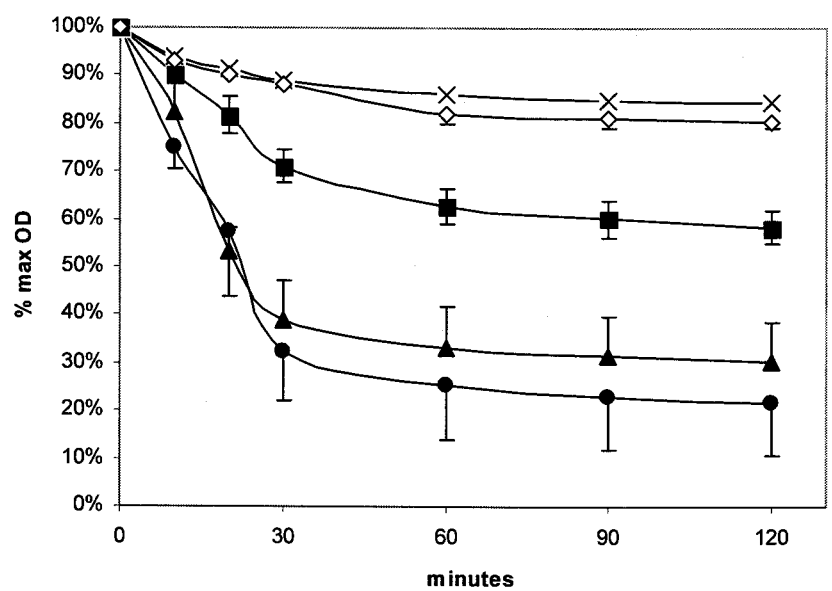

FIG. 12: Bacterial agglutination by GL-13 peptides. *P. aeruginosa* (OD 675 nm 0.6) was incubated with GL-13-OH (filled squares), GL-13-NH2 (filled triangles), GL-13-D/N—NH2 (filled circles), GK-7 (open diamonds) or HOAc (Crosses) for 120 min at room temperature. The OD 675 nm was recorded at the times indicated. The data are from three independent experiments were expressed as a percentage of starting OD (% max. OD) and are shown as mean±SEM (N=4-5).

Figure 13:
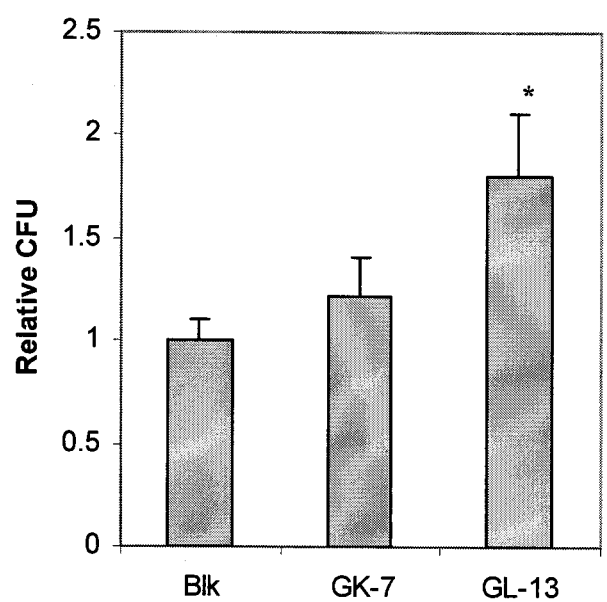

FIG. 13. Phagocytosis of *P. aeruginosa*: Bacteria ($5 \times 10^8$ CFU/ml) were incubated with buffer (Blk), GK-7 or GL-13 (100 μg/ml) for 1 h and added to RAW cells for 2 h. The RAW cells were washed and incubated with 100 μg/ml gentamicin for 90 min. The cells were lysed in 1% Tween-20 and the diluted contents plated on agar. CFU were enumerated and expressed relative to the mean of the blank in each of three experiments (N=9)*) P=0.025.

Figure 14:
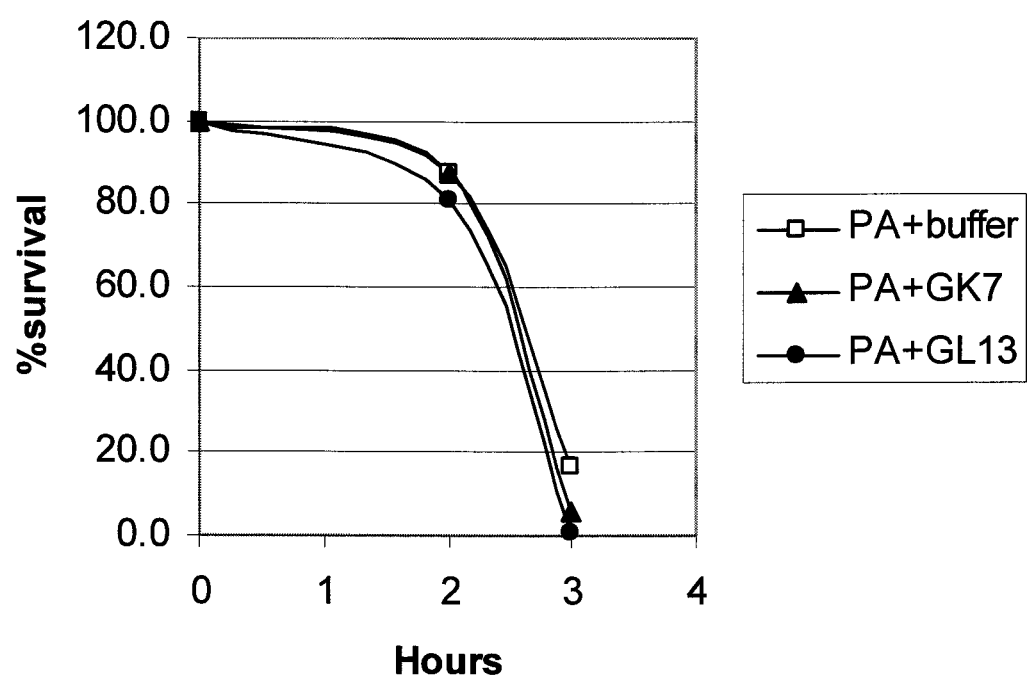

FIG. 14. Cyanide poisoning of *C. elegans*. *P. aeruginosa* kills *C. elegans* by the virulence factor cyanide (fast-kill). Worms were incubated with *P. aeruginosa* in LB for 3 h in the presence or absence of the PSP peptides GK-7 or GL-13. Total (20-40 worms per sample) and live worms were counted at each time point. The data are the mean of 4 samples for each condition. The PSP peptides did not inhibit fast killing of *C. elegans* by *P. aeruginosa* cyanide production.

Figure 15A:
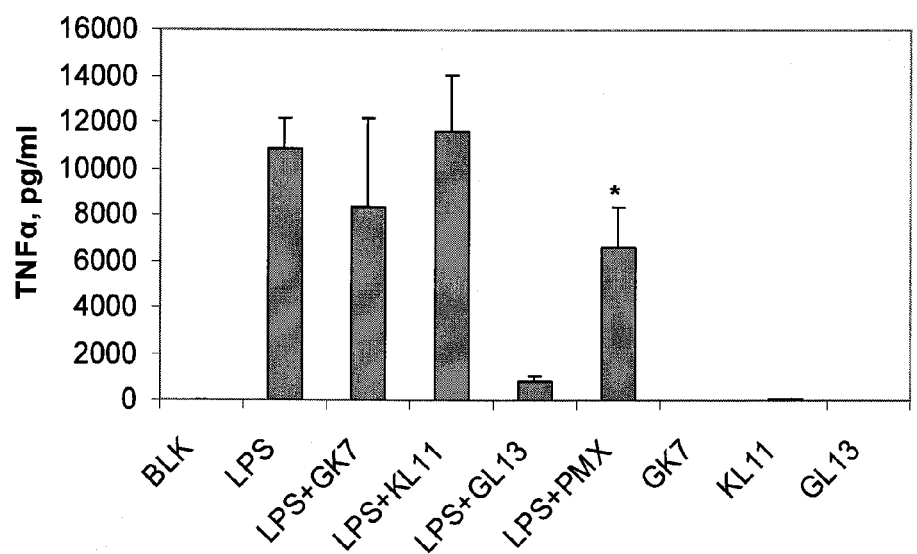
Figure 15B:
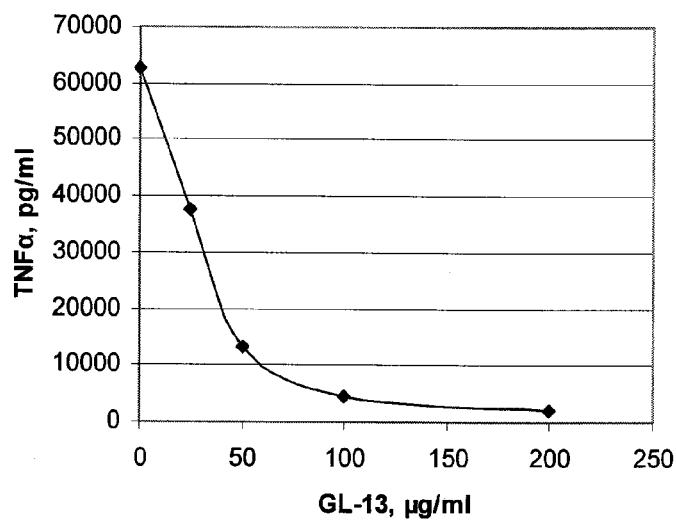

FIGS. 15A and 15B. FIG. 15A. Inhibition of endotoxin-stimulated TNFα secretion. RAW 264.7 macrophage cells were stimulated with 100 ng/ml LPS in the presence or absence of the PSP-derived peptides GK7, KL11 or GL13 (200 μg/ml). Polymyxin B (PMX) was used as a positive control. Further controls consisted of peptides alone without LPS stimulation. TNFα secretion was analyzed by ELISA of the RAW culture medium. The data are from triplicate RAW culture dishes for each condition. *) different from LPS alone P<0.03, **) P<0.0002. FIG. 15B. Dose response curve for the inhibition of LPS-induced TNFα secretion by GL-13.

Figure 16:
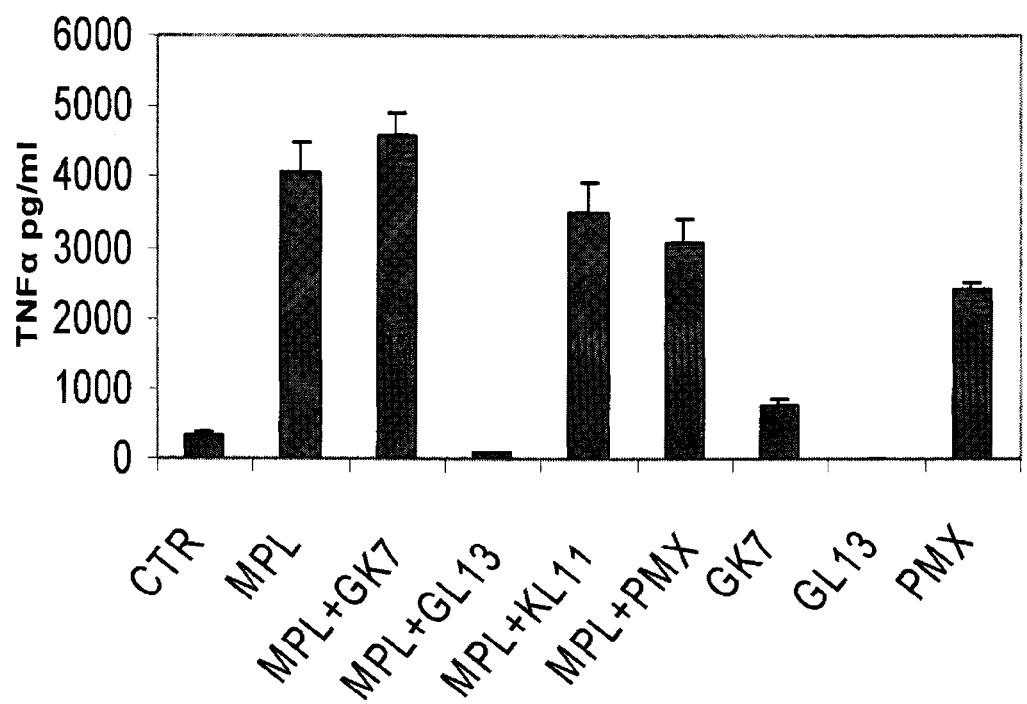

FIG. 16. PSP peptides inhibit monophosphoryl-lipid A (MPL)-induced TNFα secretion from RAW 264.7 macrophage cells.

Figure 17:
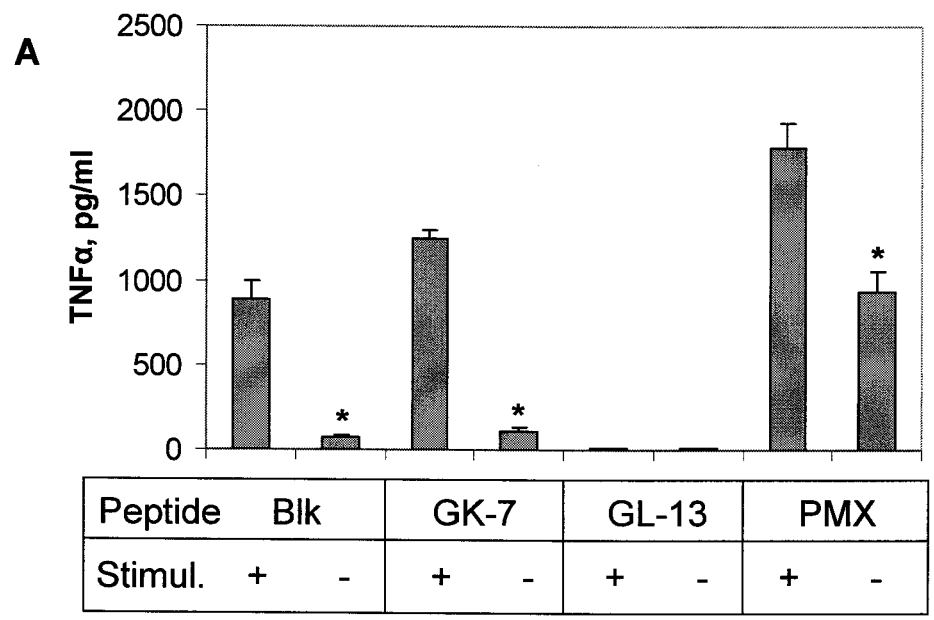
Figure 17:
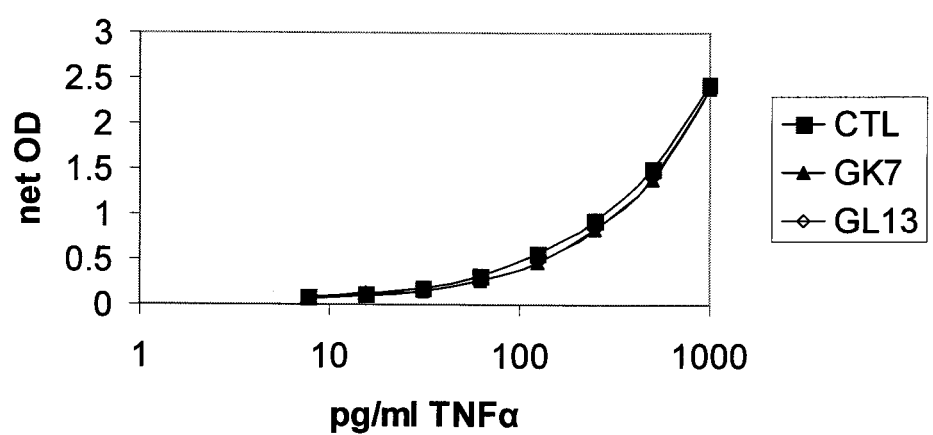

FIGS. 17A and 17B. PSP peptides inhibit phorbol ester. PSP peptides inhibit TNFα secretion from RAW 264.7 macrophage cells. 17A. RAW cells were stimulated with 100 nM Phorbol 12,13 didecanoate (+) or the inactive 4α-PDD (−) in the presence or absence of PSP peptides (200 µg/ml) or the anti-inflammatory peptide polymyxin B (PMX). GL-13 strongly inhibits the phorbol ester-stimulated secretion of TNFα. 17B. The effect of GL-13 was not a direct inhibition of the TNFα ELISA, since the ELISA standard curve was not affect by the presence of GL-13 or GK-7.

Figure 18:
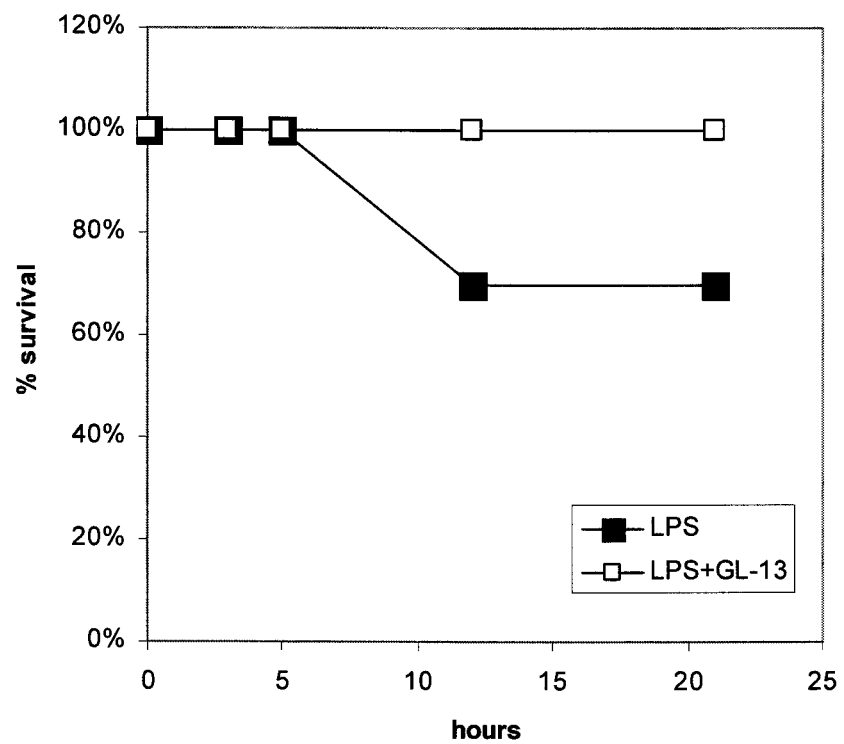

FIG. 18. GL-13 Protects Mice in an LPS Sepsis Model. C57BL/6 mice were sensitized with D-galactosamine and injected with 100 ng/mouse (50 µg/kg) of P. aeruginosa LPS that had been preincubated for 1 h RT with or without 100 µg/mouse of GL-13. Controls received LPS and 0.9% saline. The mice were observed at the times indicated and % survival calculated. The results are from two independent experiments. After 12 hours, survival in the LPS+GL-13 group was significantly different from the LPS group, $P<0.04$ (N=10).

Figure 19:
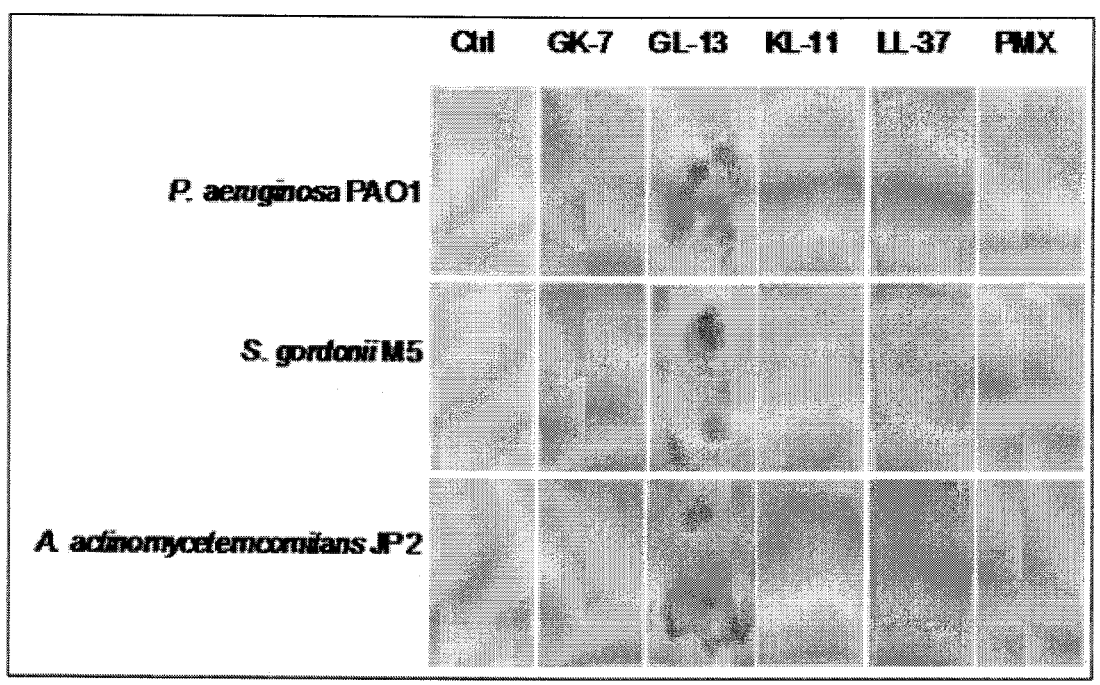

FIG. 19: Bacterial agglutination. To directly visualize bacterial agglutination, three different species P. aeruginosa (Gram−), Streptococcus gordonii (Gram+) and Aa (Gram −) were incubated with different peptides. Bacteria were stained with crystal violet to visualize the agglutinated bacteria.

Figure 20:
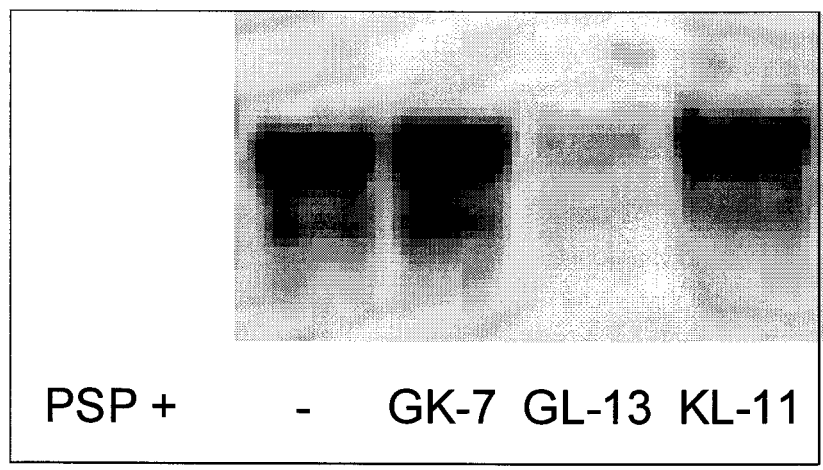

FIG. 20. Binding of PSP to LPS Sepharose. Saliva was incubated with LPS-Sepharose in the presence or absence of PSP peptides. Beads were washed and analyzed for bound PSP by immunoblotting. GL-13 inhibits binding of PSP to LPS.

Figure 21:
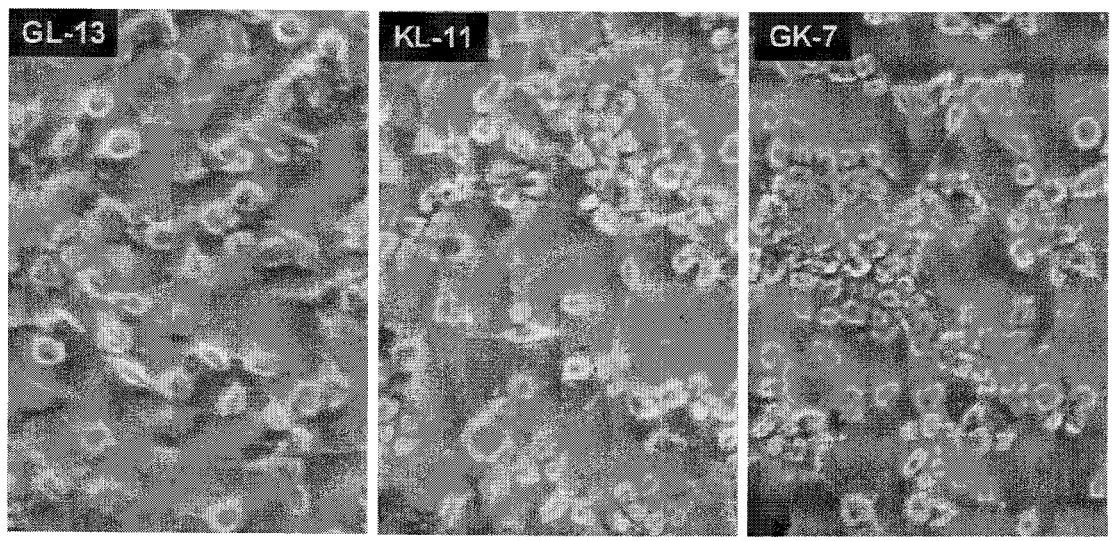

FIG. 21: RAW Cell Viability. RAW 264.7 cells were incubated with 200 ng/ml of PSP peptides for 24 h. At the end of the incubation period the cells were stained with trypan blue and photographed in the light microscope. No significant cell death was detected with any of the peptides.

Figure 22:
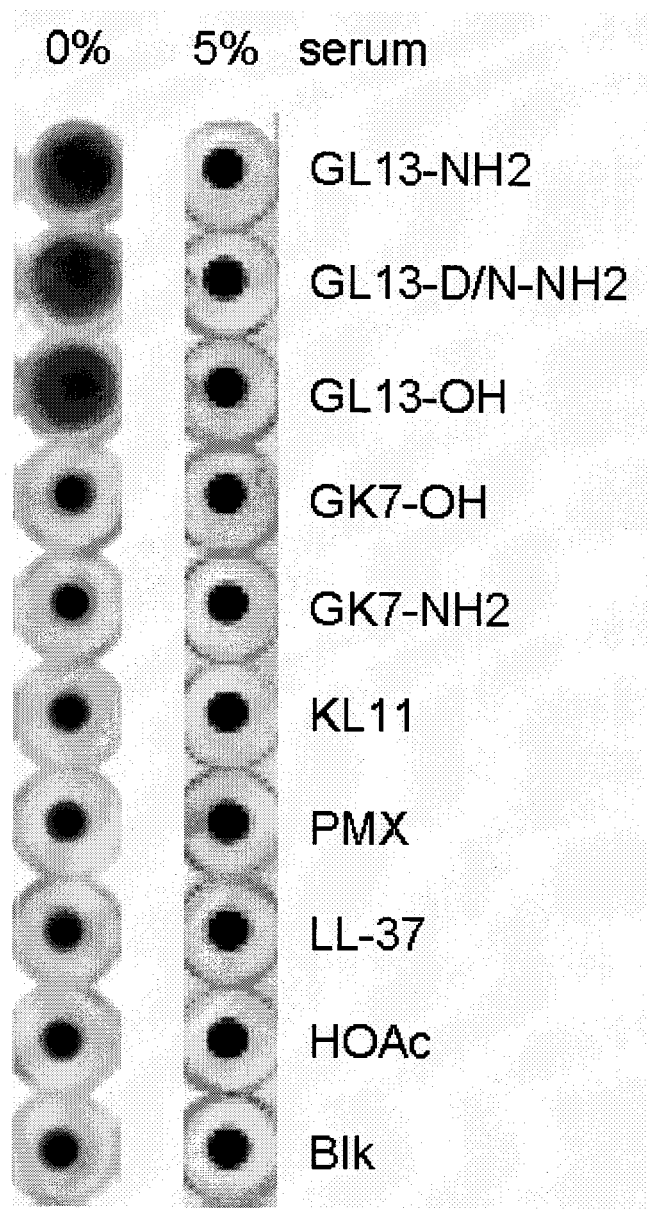

FIG. 22: Hemagglutination of sheep red blood cells. RBCs were washed in PBS and incubated for 2 h in microtiter plates in PBS±5% fetal calf serum. Peptide concentrations were 83 ng/ml. The microtiter plate was imaged. Agglutinated red blood cells form a wide mat of cells, while non-agglutinated cells form a button shaped pellet.

Figure 23A:
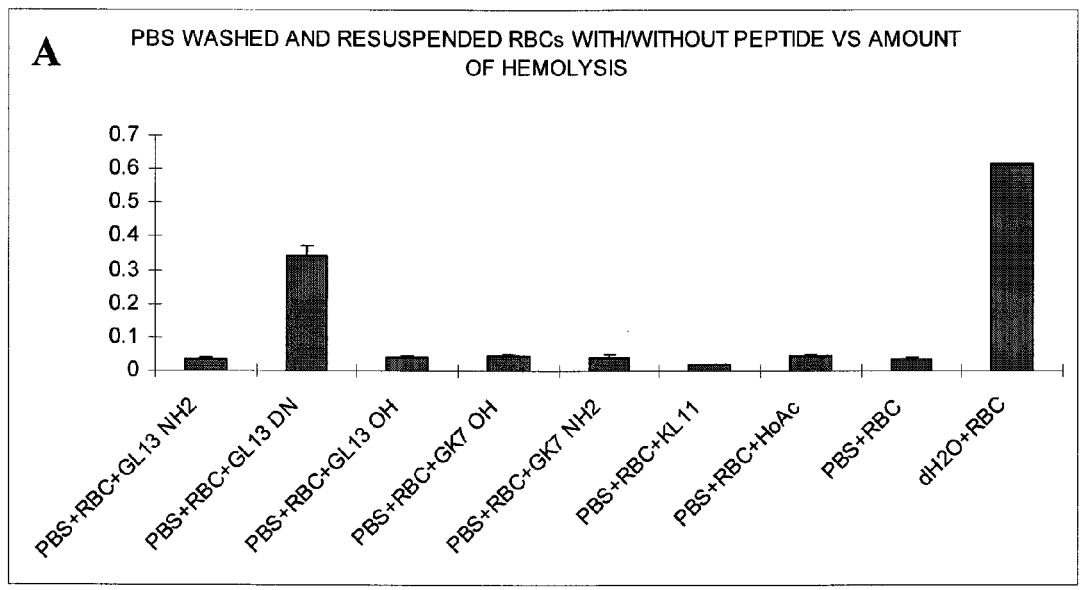
Figure 23B:
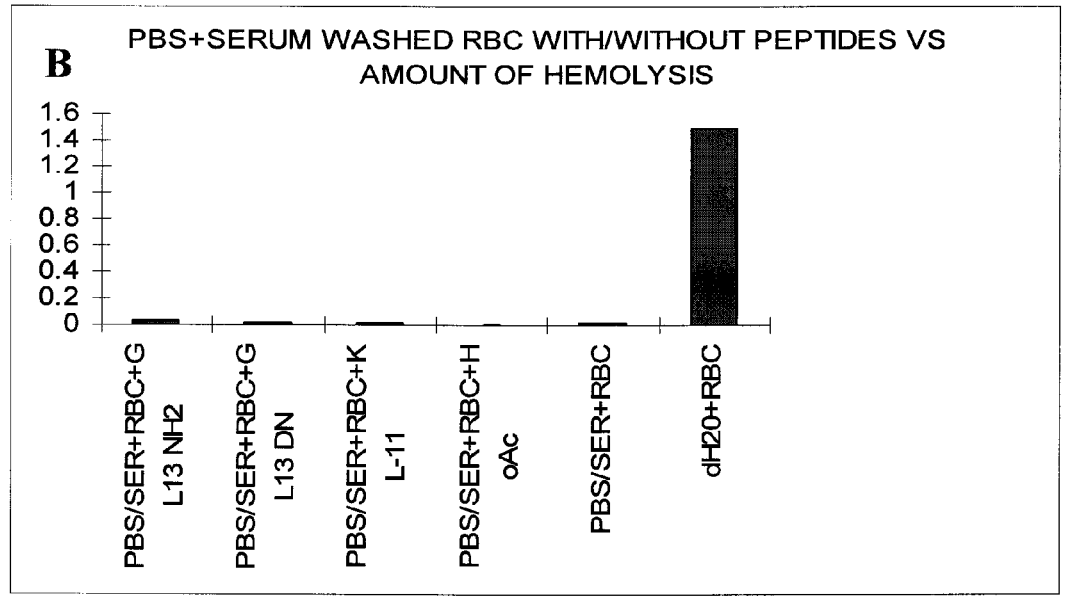

FIGS. 23A and 23B: Hemolysis of sheep red blood cells in PBS (FIG. 23A) or PBS with 5% fetal calf serum (FIG. 23B). Peptides were added at a concentration of 100 ng/ml. Samples were incubated for 2 h followed by centrifugation. Hemolysis was quantitated by the absorbance of hemoglobin at 541 nm in the supernatant fraction. Maximum lysis was observed when RBCs were incubated in dH2O. Data are presented as the mean±SEM, N=3-6. GL-13-D/N—NH2 showed hemolytic activity in the absence of serum. None of the peptides showed lytic activity in the presence of 5% serum.

DETAILED DESCRIPTION

The innate immune system produces a variety of antimicrobial proteins that serve as a first line of defense against bacterial, viral and fungal infections. Human host-defense proteins include lysozyme, lactoferrin, secretory leukoprotease inhibitor, beta defensins, alpha defensins (human neutrophil peptides), histatins, calgranulin A and B and the human cathelicidin hCAP18 (LL37) (LLGDFFRK-SKEKIGKEFKRIVQRIKDFLRNLVPRTES, SEQ ID NO:10). Many of these proteins are cationic and it has been found that depletion of cationic proteins from airway fluid eliminates its antibacterial activity. In addition to these established antimicrobial proteins, a new gene family of potential antimicrobial proteins was identified on human chromosome 20q11. The corresponding proteins are related to several previously known animal proteins, including mouse PLUNC, bovine BSP30, and rodent PSP. Several investigators have noted that the PLUNC family proteins appear to be structurally related to the antibacterial and anti-inflammatory protein Bactericidal Permeability-Increasing protein (BPI) and LPS-binding protein (LBP). The inventor tested the hypothesis that peptides based on the PSP sequence are antibacterial to the opportunistic pathogens P. aeruginosa and A. actinomycetemcomitans, which infect the airways and oral cavity.

A "biofilm" is a complex organization of bacteria that are anchored to a surface via a bacterially extruded exopolysaccharide matrix, and grow into differentiated towers that can be several hundred bacteria in height. The extruded exopolysaccharide matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because or a lack of accessibility by immunoglobulin and complement. The attachment of bacteria to a surface triggers the expression of a cassette of genes, which results in the formation of a biofilm. A "biofilm phenotype" confers to a bacterium a reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces. Biofilm bacteria have been demonstrated to be highly resistant to growth in standard planktonic (i.e., free-floating) culture, attributed to differences in gene expression.

Pharmaceutical Compositions

The compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful as antibiotics. Examples of such agents include a protein synthesis inhibitor, a cell wall growth inhibitor, a cell membrane synthesis inhibitor, a nucleic acid synthesis inhibitor, or a competitive enzyme inhibitor. In certain embodiments, the additional agent is an antibiotic such as penicillin, ampicillin, amoxicillin, vancomycin, cycloserine, bacitracin, cephalosporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimetoprim, isoniazid, paraaminosalicylic acid, or ethambutol.

In certain embodiments, the compound of the invention is contacted with a microbe.

Accordingly, in one embodiment the invention also provides a composition comprising a compound of the present invention, at least one other therapeutic agent, and a pharmaceutically acceptable diluent or carrier. The invention also provides a kit comprising a compound of the present invention, at least one other therapeutic agent, packaging material, and instructions for administering the compound of the present invention or the pharmaceutically acceptable salt thereof and the other therapeutic agent or agents to an animal to prevent bacterial infection.

In certain embodiments the peptide of the present invention is produced as a fusion protein of the peptide sequence and a carrier protein. The carrier protein can subsequently be cleaved to release the active peptide. Phage display of active peptides may also be a useful method to present the peptide to cells.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an a-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

In certain embodiments, the peptides are modified by C-terminal amidation, head to tail cyclic peptides, or containing Cys residues for disulfide cyclization, siderophore modification, or N-terminal acetylation.

The term "peptide" describes a sequence of 7 to 50 amino acids or peptidyl residues. Preferably a peptide comprises 7 to 25, or 7 to 15 or 7 to 13 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

By "variant" peptide is intended a peptide derived from the native peptide by deletion (so-called truncation) or addition of one or more amino acids to the N-terminal and/or C-terminal end of the native peptide; deletion or addition of one or more amino acids at one or more sites in the native peptide; or substitution of one or more amino acids at one or more sites in the native peptide. The peptides of the invention may be altered in various ways including amino acid substitutions, deletions, truncations, and insertions. Methods for such manipulations are generally known in the art. For example, amino acid sequence variants of the peptides can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell or bacteriophage. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression, cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a known mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world-wide-web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about 5 EC lower than the $T_m$ for the specific sequence at a defined ionic strength and pH.

An example of highly stringent wash conditions is 0.15 M NaCl at 72 EC for about 15 minutes. An example of stringent wash conditions is a 0.2×SSC wash at 65 EC for 15 minutes. Often, a high stringency wash is preceded by a low stringency wash to remove background probe signal. An example medium stringency wash for a duplex of, e.g., more than 100 nucleotides, is 1×SSC at 45 EC for 15 minutes. An example low stringency wash for a duplex of, e.g., more than 100 nucleotides, is 4-6×SSC at 40 EC for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30 EC and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The invention will now be illustrated by the following non-limiting Examples.

Example 1

Anti-Bacterial Paraotid Secretory Protein (PSP) Peptides

Parotid Secretory Protein (PSP) is a potential host-defense protein expressed in the oral cavity and upper airways. The protein is structurally related to bactericidal/permeability-increasing protein, suggesting that PSP also exhibits antibacterial activity and could be a source of novel antibacterial peptides.

Potential antibacterial PSP peptides were designed based on the predicted structure of PSP. The bactericidal activity of these peptides was tested in vitro against *Pseudomonas aeruginosa* PAO1 and *Aggregatibacter (Actinobacillus) actinomycetemcomitans* JP2. Anti-pseudomonal activity was also tested in vivo in the Romaine lettuce model. MIC of the peptides for *P. aeruginosa* and *A. actinomycetemcomitans* were tested using the microdilution method. The effect of PSP peptides on bacterial agglutination and biofilm formation were tested in polypropylene and PVC microtiter plate assays, respectively.

*P. aeruginosa* was the most susceptible to the PSP peptides. A 13-mer peptide GL-13 killed 90% of *P. aeruginosa* in 2 h at a concentration of 10 µg/ml. None of the peptides exhibited an MIC, suggesting that they are not bacteriostatic. GL-13 modulated the agglutination of both *P. aeruginosa* and *A. actinomycetemcomitans*. Biofilm assays revealed that GL-13 inhibits *P. aeruginosa* biofilm formation but the peptide cannot eliminate biofilm once it is formed.

PSP peptides are differentially bactericidal to *P. aeruginosa* and *A. actinomycetemcomitans* but do not exhibit bacteriostatic activity. Biofilm formation is inhibited by PSP peptides.

Methods

Bacterial Culture Conditions.

*Pseudomonas aeruginosa* PAO1 (ATCC) were maintained on *Pseudomonas* Isolation Agar while *Aggregatibacter (Actinobacillus) actinomycetemcomitans* JP2 were maintained on Brain Heart Infusion (BHI) agar (Difco) containing 0.5% yeast extract and 0/4 mg/L of $NaHCO_3$. Overnight cultures of PAO1 were incubated at 37° C. in Luria Bertani (LB) broth (Difco). JP2 were cultured under reduced oxygen conditions in BHI broth containing 0.5% yeast extract and 0.4 mg/L $NaCO_3$ in a GasPak 100 container (Becton Dickinson) at 35° C.

Peptides.

PSP peptides were designed as described below. GK7 and KL11 were unmodified while GL13 was C-terminally amidated. The peptides were purchased from Peptides International, Louisville, Ky., LL37 was from Innovagen, Lund, Sweden or Bachem/Peninsula, San Carlos, Calif. Lysozyme (egg white) was from Fisher Scientific. Peptide stock solutions (1 mg/ml) were prepared in 0.01% acetic acid and stored at −20° C.

Assay for Bactericidal Activity In Vitro.

Overnight cultures of bacteria were pelleted and resuspended in 10 mM sodium phosphate, pH 7.4 ($10^5$ CFU/ml). Diluted bacteria (100 µl) were incubated with 10 or 100 µg/ml of each peptide in 10 mM sodium phosphate, pH 7.4. *P. aeruginosa* PAO1 were incubated for 2 h at 35° C. while *A. actinomycetemcomitans* JP2 were incubated for 4 h at 37° C. under reduced oxygen conditions. Bacterial cultures were diluted and plated on LB agar (*Pseudomonas*) or BHI agar plates (low oxygen incubation) and surviving CFUs enumerated after 1-2 days at 35° C.

Assay for Antibacterial Activity In Vivo.

Romaine lettuce heads were purchased from local grocery stores. Outer leaves were removed and undamaged leaves were selected. The leaves were rinsed in 0.1% bleach and incubated in plastic containers on filter paper moistened with 10 mM $MgSO_4$. Overnight cultures of *P. aeruginosa* were diluted to $10^8$ CFU/ml in 10 mM $MgSO_4$ and supplemented with 200 µg/ml of each peptide. Ten µl ($10^6$ CFU, 2 µg peptide) were injected into the midrib of each leaf using a micro pipetter. Blank controls were incubated with buffer only, and bacterial controls were incubated without peptide. The plastic trays were covered and incubated at 35° C. Leaves were inspected daily for browning around the injection site or along the midrib. Generally rotting or moldy leaves were discarded. Infection was scored on a scale from 0% to 100% relative to blank controls and bacterial controls, respectively.

MIC Determination:

The minimal inhibitory concentration (MIC) of PSP peptides was tested using the broth dilution assay. Briefly, overnight cultures of bacteria were diluted in Mueller-Hinton broth (MHB) (Difco) to $10^5$ CFU/ml. Diluted bacteria (100 µl) and two-fold serial dilutions of peptides in 10 mM sodium phosphate, pH 7.4 (20 µl) were mixed in polypropylene microtiter plates and incubated for 24 h at 35° C. for *P. aeruginosa* or 48 h at 37° C. under reduced oxygen conditions for *A. actinomycetemcomitans*. Control samples were incubated with bacteria and two-fold serial dilutions of 20 µl 0.01% acetic acid in 10 mM sodium phosphate. Bacterial growth was quantitated by the optical density (OD) at 570 nm. A Kodak CF440 image station was used to record bacterial pelleting in the wells.

Biofilm Assays:

Overnight cultures of *P. aeruginosa* PAO1 were diluted 1:100 in MHB and 100 µl/well were incubated with 5 µl of LL-37, GK-7, GL-13, KL-11 or lysozyme (1 mg/ml) in PVC microtiter plates. The plates were incubated for 6 h at 32° C. under aerobic or reduced oxygen conditions. Bacterial growth was quantitated spectrophotometrically at 570 nm. Twenty-five µl of 1% crystal violet in $dH_2O$ was added to each well and incubated 20 min at room temperature. The wells were emptied and washed three times in $dH_2O$ and then incubated for 30 min with 200 µl of 95% ethanol. The OD at 570 nm was determined as a measure of biofilm formation. Growth and biofilm values were normalized against the mean of samples incubated with 0.01% acetic acid without peptides.

For biofilm elimination experiments, PVC microtiter plates were pre-incubated with bacteria for 4 or 6 hours, followed by washing and incubation with peptides (50 µg/ml) for 2 h. Remaining biofilm was quantitated by crystal violet staining as above.

*A. actinomycetemcomitans* biofilms were produced in polypropylene microtiter plates that were incubated with *A. actinomycetemcomitans* ($10^5$ cells/ml) for 48 h at 35° C. in MHB (FIG. 8). The plates were rinsed in PBS and stained with Coomassie blue. Following a wash step the dye was dissolved in 95% ethanol and quantitated spectrophotometrically at 570 nm.

Statistics.

Data are expressed as mean±SEM. Treated and untreated samples were compared by unpaired Student's t-test, $P<0.05$ was considered statistically significant.

Results

Design of PSP Peptides.

Figure 2:
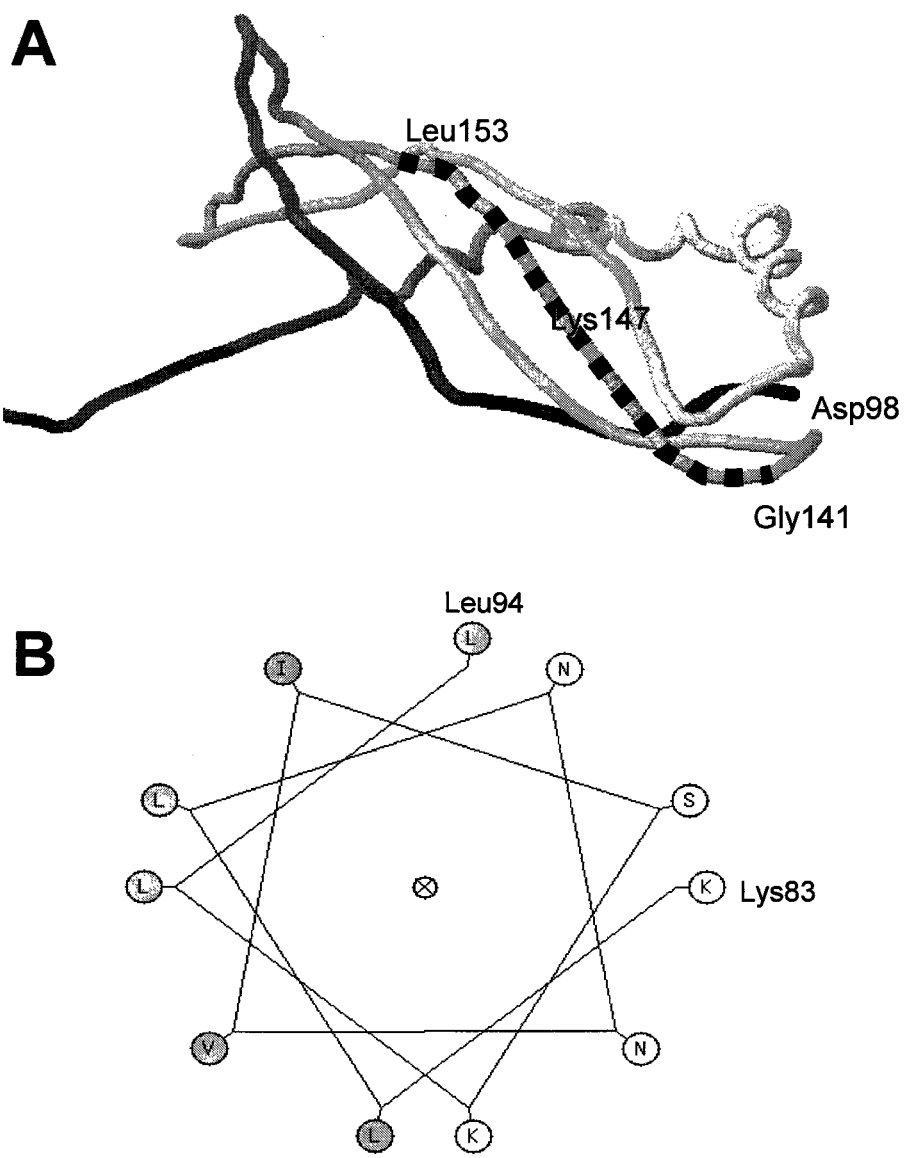
FIGS. 2A-2D: Structure of PSP and PSP peptides. A: Structural model of hPSP. The locations of GK7 and GL 13 are shown as the broken line with the positions of the terminal amino acids indicated. KL11 is not modeled in this view (N-terminal residue is ASP98). B: Helical wheel representation of KL11. Hydrophobic residues are shaded. The locations of the N-terminal Lys and C-terminal Leu residues are indicated. C: Alternate side view of hPSP. D: Alternate end view of hPSP.

The inventors previously described the anti-inflammatory activity of three synthetic PSP peptides, GK7, KK9 and KN11. For this study, GK7 and an extended version, designated GL13, were tested, as well as an extended version of KK9, termed KL11. The location of each peptide in the hPSP sequence is shown in FIG. 1. In previous work, the inventors used the 3D-PSSM program to model the PSP structure (see FIGS. 2C and 2D, and Geetha C et al., *J Dent Res* 2005; 84: 149-53). Since 3D-PSSM has been replaced by Phyre (on the world-wide-web at sbg.bio.ic.ac.uk/~phyre/), the inventors reanalyzed the PSP sequence using this program. The top model (95% estimated precision) was again based on the structure of BPI (PDB: d1ewfa1). This model included residues 98-237 of hPSP. A similar model was obtained with the BPI structure PDB: c1bp1. The 1ewfa1-model was visualized using Firstglance for Jmol (on the world-wide-web at firstglance.jmol.org). FIG. 2A shows the position of peptides GK7 and GL13 in this model. Peptide KL11 is not included in the new model. A helical wheel projection of KL11 reveals a potential amphipathic helix suggesting that KL11 may be an antibacterial peptide (FIG. 2B).

Bactericidal Activity

Figure 3A:
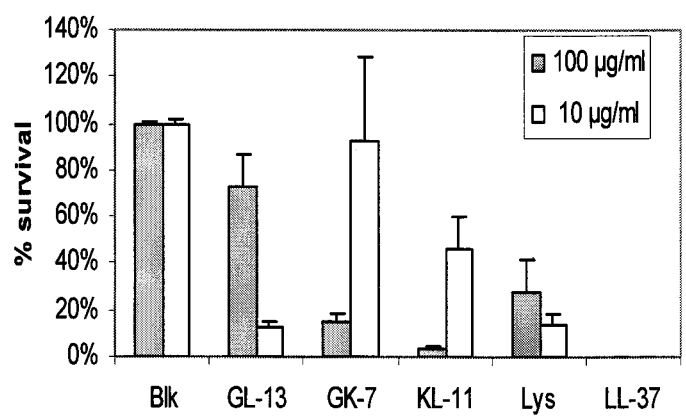
FIGS. 3A and 3B: PSP peptides exhibit bactericidal activity in vitro. The PSP peptides GL13, GK7 and KL11, lysozyme, LL37 or no peptide (BLK) were incubated with *P. aeruginosa* (FIG. 3A) or *A. actinomycetemcomitans* (FIG. 3B). *P. aeruginosa* PAO1 ($10^5$ cells/ml) were incubated for 2 h at 35° C. with 10 µg/ml (open bars) or 100 ng/ml (shaded bars) of each peptide. *A. actinomycetemcomitans* JP2 ($10^5$ cells/ml) were incubated for 4 h at 37° C. under reduced oxygen conditions. Bacterial cultures were diluted and plated on LB agar (Pseudomonas) or BHI agar plates (A.a., low oxygen incubation) and surviving CFUs enumerated. The data are shown as mean±SEM, *P. aeruginosa*: N=8-22 at 100 ng/ml, N=2-10 at 10 μg/ml. *A. actinomycetemcomitans*: N=3. *) P<0.0001, ) P<0.004, *) P<0.02
Figure 3B:
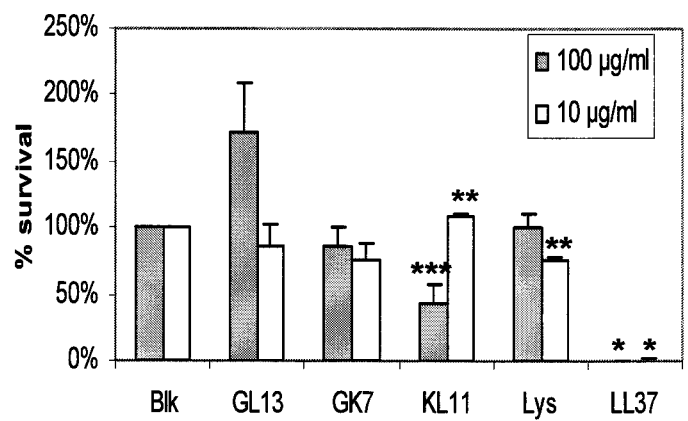

The predicted structural similarity of PSP and BPI suggested that PSP functions as an antibacterial protein. In preliminary experiments the inventors found that intact PSP did indeed kill *P. aeruginosa*. To test if the PSP peptides are antibacterial, each peptide was incubated with *P. aeruginosa* or *A. actinomycetemcomitans* for 2 and 4 hours, respectively. Surviving bacteria were enumerated as CFU on agar plates (FIGS. 3A and 3B). Each PSP peptide killed *P. aeruginosa* at either 10 or 100 µg/ml. Only KL11 was bactericidal to *A. actinomycetemcomitans* and the effect was minor (40% survival). For each species the activity of the PSP peptides was similar to that of the established antimicrobial protein lysozyme, whereas the human cathelicidin peptide LL37 exhibited 100% killing under the conditions used here.

The in vitro assay suggested that PSP peptides are antibacterial but of intermediate activity, similar to that of lysozyme. To determine if the PSP peptides were active in vivo, a lettuce infection model was used. This model for *P. aeruginosa* infection shares virulence factors with animal models. The bacteria were mixed with each peptide and injected into small depressions of the midrib of lettuce leaves. After 2-3 day incubation the infections were scored by the extent of browning of the leaves surrounding the injection sites. GL13, KL11 and lysozyme significantly reduced the infection of lettuce leaves (FIG. 4), while neither GK-7 nor LL37 showed a significant effect on infection.

To determine if the PSP peptides exhibit bacteriostatic activity, broth dilution assays were performed. Two-fold serial dilutions, starting at 84 µg/ml were performed for GK7, GL13, KL11, LL37 and lysozyme (FIGS. 5A and 5B). LL37 exhibited an MIC of 42 µg/ml for *P. aeruginosa*. Lysozyme reduced growth of *P. aeruginosa* by about 50% but did not exhibit a defined MIC. LL37 and lysozyme did not inhibit growth of *A. actinomycetemcomitans*. None of the PSP peptides inhibited growth of *P. aeruginosa* or *A. actinomycetemcomitans* in this assay, suggesting that these peptides are not bacteriostatic. A combination of LL37 and lysozyme or GL13 and lysozyme had no effect beyond that of the peptides individually.

Anti-Biofilm Activity

Bacterial pellets formed in the wells of the 96-well plates during the broth dilution assays. Interestingly, GL13 caused the appearance of a diffuse pellet as compared to the small round pellets seen with other peptides for both *A. actinomycetemcomitans* and *P. aeruginosa*. The diameter of the bacterial pellet was directly dependent on the concentration of GL-13 (FIGS. 6A-6C). This result suggested that GL-13 could affect bacterial adhesion and biofilm formation. To test this, *P. aeruginosa* were incubated in PVC microtiter plates and the adhered cells stained with crystal violet. FIG. 7A shows that GL13 and KL11 inhibited biofilm formation by 60% and 40%, respectively, with only a small (non-significant) reduction of bacterial growth. LL37 showed strong reductions of both growth and biofilm formation while lysozyme affected neither growth nor biofilm formation under these conditions. *A. actinomycetemcomitans* biofilms were also inhibited by GL13 when the bacteria were cultured on polypropylene plates under reduced oxygen conditions (FIG. 8).

*P. aeruginosa* PAO1 biofilms are more pronounced under anaerobic conditions. Thus, the effect of PSP peptides on biofilm formation was tested under reduced oxygen conditions. The cellular effect of reduced oxygen conditions was monitored by detecting the absence of pyocyanin production. Both GL13 and KL11 reduced biofilm formation under low oxygen conditions, but the effect was less pronounced than under atmospheric conditions (FIG. 7B).

Finally, the inventors tested if PSP peptides could eliminate pre-formed biofilms. *P. aeruginosa* were incubated for 4 h or 6 h in the absence of peptides to allow biofilm formation. Non-adhered bacteria were washed away and the plates were then incubated with each peptide prior to quantitation of biofilm, as described above. FIG. 9 shows that none of the peptides eliminated pre-formed biofilms. In fact, in one case, LL37, more biofilm was retained in the presence of the peptide than with buffer alone.

Discussion

Peptides derived from PSP exhibit antibacterial activity both in vitro and in vivo. The in vitro bactericidal activity is comparable to that of lysozyme, an established antimicrobial protein in mucosal secretions. However, the peptides were less effective than the antimicrobial peptide LL37 against both *P. aeruginosa* and *A. actinomycetemcomitans*. Unlike LL37 and lysozyme, the PSP peptides did not exhibit bacteriostatic activity. The lack of bacteriostatic activity of PSP peptides was a surprise considering that GL13 and KL11 reduced the infection of lettuce leaves over several days. One possible explanation is that the lettuce leaf model does not only reflect bacterial growth but also bacterial virulence. Hence, bacterial virulence factors may be inhibited by PSP peptides in the lettuce leaves.

The peptides tested here represent three distinct regions of the PSP molecule. However, these regions are predicted to be in proximity in the folded full-length protein (see FIG. 2C). Thus, an additive effect of these domains may be found when the intact protein is tested. Alternatively, the different peptide activities could indicate that PSP contains different functional domains that represent distinct or overlapping biological activities, e.g., bactericidal activity (shown here) and the anti-inflammatory activity reported earlier (Geetha C et al., *J Dent Res* 2005; 84: 149-53). The differences in activity of GK7 and GL13 suggest that the biological activity of peptides from this region can be further modulated by modification of the peptide sequence.

GL13 affects bacterial aggregation and biofilm formation. This was seen with both *P. aeruginosa* and *A. actinomycetemcomitans* although GL13 was not bactericidal to the latter bacteria. The effects on bacterial pelleting suggest that the peptide physically prevents biofilm formation rather than killing the bacteria or inhibiting their growth in biofilms. Consistent with this view, none of the peptides were able to eliminate pre-formed biofilm. Together with the bactericidal activity of the peptides, it appears that PSP peptides can act in the early phases of infection but are not able to control growth of bacteria or eliminate biofilms, once established. Other components of host-defense must act in these later stages of infection.

Saliva and the mucosal secretions of the upper airways contain a multitude of antibacterial proteins (e.g. lactoferrin, lysozyme, LL37, and defensins). Many of these proteins, including the PSP-related protein PLUNC, are cationic and it has been found that removal of cationic proteins from human airway fluid eliminates its antibacterial activity. In this mix some proteins, e.g., LL37 exhibit strong antibacterial activity while others, e.g., lysozyme and PSP, appear to have moderate antibacterial activity. Given the broad range of microbes that enter and occupy the oral cavity and airways, this array of antimicrobial proteins likely serves to maintain bacterial homeostasis and prevent infections from taking hold. The biofilm inhibitory action of PSP appears well suited for this role as well. These proteins could play an important role in protecting the mucosal surfaces.

Example 2

Methods of Reducing Oral Inflammation

Parotid secretory protein (PSP) is expressed in human salivary glands and gingival epithelial cells in response to bacterial or inflammatory stimulation. As discussed in Example 1 above, PSP is antibacterial to the Gram-negative bacteria *Aggregatibacter* (*Actinobacillus*) *actinomycetemcomitans* and *P. aeruginosa*. PSP binds lipopolysaccharides (LPS) and PSP peptides block the activity of LPS in standard assays of inflammation.

The oral cavity is a major entry-point for bacteria, viruses and other microbial pathogens. Accordingly, saliva and oral tissues express multiple anti-microbial proteins that act as host-defense factors in the oral cavity. Lysozyme, cathelicidins, histatins, lactoferrin and defensins are examples of antimicrobial proteins found in the mouth. These components of innate immunity confer rapid protection from pathogens, prior to or during the development of an acquired immune response. The large variety of antimicrobial proteins expressed in oral epithelial tissues presumably allows for an effective innate immune response to the large variety of microorganisms that invade the mouth. Indeed, different oral bacteria elicit distinct transcription profiles in oral epithelial cells. It would follow that different antimicrobial molecules are induced by different microbial challenges and in different parts of the oral cavity and upper respiratory tract in order to target pathogens in their particular ecological niches. Identification of these components of oral mucosal immunity is an important step in controlling oral infections. As antibiotic resistance is a growing problem, the identification of novel antimicrobial treatments, based on the body's natural defenses, is of particular interest.

Inflammation is part of the natural defense to an infection. However, in the mouth this beneficial inflammation may progress to the oral inflammatory diseases gingivitis and periodontitis. Inflammation may be triggered by bacteria, free endotoxins, tobacco or other irritants or allergens. The gram-negative bacteria *Porphyromonas gingivalis, Aggregatibacter* (*Actinobacillus*) *actinomycetemcomitans, Tannerella forsythia* and *Treponema denticola* have all been associated with the development of periodontitis. LPS expressed by Gram-negative bacteria activate macrophages and oral epithelial cells causing an inflammatory response that includes the release of inflammatory cytokines and NO. Cytokines also play a role in the switch from the initial innate immune response to a sustained adaptive immune response. Suppression of a prolonged inflammatory response is an important factor in reducing the progression to inflammatory diseases.

A better understanding of anti-bacterial and anti-inflammatory proteins and their function in the inflammatory cascade is critical for enhanced treatment options of oral inflammatory diseases. The inventors recently observed that PSP is expressed in the oral cavity (parotid gland, saliva and gingival epithelial cells) and that this protein exhibits antibacterial and anti-inflammatory activities. Thus, the present experiments test hypotheses that PSP directly combats microbial growth and colonization (bacterial growth inhibition activity and attenuation of bacterial invasion of epithelial cells), modulates pathogen recognition (LPS-binding activity), and modulates inflammatory signals (LPS-induced cytokine secretion).

Parotid Secretory Protein (PSP) was originally identified in the mouse parotid gland and it has long been recognized as a major secretory protein in rodent parotid glands. PSP is also expressed in the mouse lacrimal gland and in neonatal rat submandibular glands. Related proteins are found in bovine saliva and porcine and hamster parotid glands. A human PSP cDNA sequence was also reported in the patent literature, although the human protein was not characterized at the time.

Comparison of the rat PSP sequence to the sequence of human of chromosome 20 revealed the location of the putative human PSP gene (C20orf70, SPLUNC2). The inventors cloned the corresponding cDNA from human parotid tissue (Genbank Accession Number AF432917) and noted that PSP is also expressed in human saliva and gingival epithelial cells. In the latter cell type, PSP expression is regulated by the Gram-negative bacteria *P. gingivalis* and the pro-inflammatory cytokine TNFα.

PSP is a dual function antibacterial and anti-inflammatory protein that plays a role in the innate immunity of the oral cavity. PSP is an early responder to bacterial infection and subsequently acts to control the mucosal inflammatory response, possibly modulated by proteolytic processing. This model is supported by the inventors' findings that PSP in the oral cavity is secreted into saliva and is expressed in oral epithelial cells where its expression is directly regulated by both bacteria and pro-inflammatory cytokines.

PSP Binds LPS:

PLUNC binds LPS, as expected from its structural similarity to LPS-Binding Protein (LBP). To determine if PSP also binds LPS, the protein was expressed in GH4C1 cells and the secretion medium was used for affinity chromatography on LPS-Sepharose. After binding, the affinity matrix was washed and then eluted with PBS+0.2 g/l EDTA. PSP was quantitatively retained by the LPS affinity matrix and eluted by EDTA. The results of this experiment establish that PSP is an LPS-binding protein and provides a method for purification of PSP.

PSP Peptides Inhibit LPS Binding to LBP:

Analysis of the PSP sequence indicated three possible regions of biological activity. Initially, three peptides corresponding to the PSP sequence in these regions were designed and used in these studies. The initial step in the inflammatory cascade is the binding of LPS to LPS-binding protein. This binding was inhibited by preincubation of LPS with each of the three peptides. Strong inhibition was also observed with polymyxin B, while the antibacterial cationic peptide substance P had no effect on LPS binding to LBP (Table 1). The binding of LPS to LPB was analyzed to ELISA. 0% inhibition (100% binding) was determined in the absence of inhibitors while 100% inhibition was determined in the presence of the inhibitor polymyxin B. The inhibition of each peptide is determined relative to the effect of polymyxin B.

TABLE 2

| Peptide | Inhibition (Mean ± SEM) | N |
|---|---|---|
| KN11 | 36% ± 13 | 7 |
| KK9 | 34% ± 12 | 7 |
| GK13 | 21% ± 9 | 7 |
| Substance P | −18% ± 19 | 5 |

PSP Peptides Inhibit TNFα Secretion:

The inventors previously found that PSP peptides can inhibit the LPS-induced secretion of TNFα from the macrophage cell line RAW264.7, a model for inflammatory response. In the present experiments, the redesigned PSP peptides (GL13, KL11) were tested for their effect on TNFα secretion and compared to GK7. FIG. 15A shows that GL13 strongly reduced (about 11-fold) this inflammatory response on RAW cells. In contrast, the peptides alone did not strongly stimulate TNFα secretion, suggesting that they do not elicit an inflammatory response.

Modification Of PSP Peptides:

Three PSP peptides were designed and tested for anti-inflammatory activity, as described in Geetha et al., 2005 (supra). The peptides blocked LPS action on macrophages and the binding of LPS to LBP, although the effect was not strong (see Table 2). In an attempt to optimize biological activity, the two most promising peptides (KK9 and GK7) were modified by C-terminal extension to generate KL11 and GL13, respectively. The goal was to produce peptides with an optimized amphipathic helix and to incorporate the optimal number of hydrophobic and charged residues. The results described above show that the activity of GL13 differs from the shorter peptide GK7 (FIGS. 4, 7, 10, 11, 13 and 15A).

Epithelial Invasion Assays:

To determine if PSP peptides prevent the penetration of epithelial cell monolayers, the epithelial cell line MDCK was cultured on permeable membrane filters. P. aeruginosa were added to the apical medium of confluent MDCK cell monolayers and bacterial penetration was determined as the number of bacteria recovered from the basolateral medium after a 24 h incubation. FIG. 10 shows that GL13 and KL11 could inhibit the penetration of P. aeruginosa on MDCK cell monolayers.

As a second model epithelial cell line, the immortalized rat parotid cell line PAR C5 is used. PAR C5 cells are less well characterized than MDCK cells, but the related cell line PAR C10 forms polarized monolayers. In addition, the inventors have found that SEAP, a marker for apical secretion in MDCK cells, is also secreted mainly (74%) from the apical side of PAR C5 cells cultured on membrane filters.

Cell Death Assay:

The inventors have used three different assays for analysis of cytotoxicity in mammalian cells: trypan blue exclusion, propidium red uptake, and ATP production. Experiments have been performed with rat pituitary GH4C1 cells and mouse RAW 264.7 cells. The cells were incubated with PSP peptides for 24 h followed by staining with trypan blue to identify permeabilized and dead cells. Less than 10% of the cells were Trypan blue positive and no significant increase in trypan blue staining was seen in the presence of PSP peptides. Clear cytotoxicity was noted when the cells were incubated with LPS. When rat PSP was expressed in GH4C1 and PC12 cells, the inventors did not note increased cell death or loss of function, as compared to cells transfected with other proteins.

Assay for Inflammation:

To determine if the PSP peptides cause an inflammatory response in RAW 264.7 cells, the cells were incubated with each peptide for 24 h and TNFα secretion was quantitated by ELISA. GK7 was the only peptide to elicit a small increase in TNFα secretion from the RAW cells (FIG. 16).

Example 3

Bacterial Agglutination

Experimental Procedures

Bacterial Culture Conditions—

All bacterial media were from Difco/Becton Dickinson. Pseudomonas aeruginosa PAO1 was maintained on Pseudomonas Isolation Agar. Broth cultures of PAO1 were grown at 37° C. in Luria Bertani (LB) medium. Aggregatibacter (Actinobacillus) actinomycetemcomitans JP2 was grown on Brain Heart Infusion (BHI) agar containing 0.5% yeast extract and 0.4 mg/L of NaHCO$_3$. Streptococcus gordonii M5 was maintained on BHI agar containing 0.5% yeast extract. S. gordonii M5 and A. actinomycetemcomitans JP2 were cultured under reduced oxygen conditions in a GasPak 100 container (Becton Dickinson) at 35° C.

Peptides—

PSP peptides (FIG. 1, Table 1) were designed as described herein in the Results section. The predicted isoelectric point and net charge at pH 7.0 of each peptide was calculated with the Peptide Property Calculator at Innovagen.com (Innovagen, Lund, Sweden). The PSP peptides were purchased from Peptides International, Louisville, Ky. LL-37 was obtained from Innovagen or Bachem/Peninsula, San Carlos, Calif. Lysozyme (egg white) was from Fisher Scientific. Polymyxin B was from Sigma. All peptide stock solutions (1 mg/ml) were prepared in 0.01% acetic acid and aliquots stored at −20° C.

Hemagglutination Assay—

Briefly, unmodified sheep erythrocytes (Cappel, MP Biomedicals, Irvine, Calif.) were washed in PBS and suspended at 1% in PBS. Diluted erythrocytes and 20 μg/ml of each peptide in PBS were mixed in polypropylene microtiter plates (120 μl per well) and incubated for 2 h at 35° C. The plates were imaged on a Kodak Image station.

Bacterial Agglutination Assays—

To visualize bacterial agglutination, overnight cultures of each species were washed and diluted to 1:100 in PBS. Peptides were added to a final concentration of 100 μg/ml and the samples incubated in a polystyrene plate at room temperature for 30 min. The bacteria were stained with crystal violet and the supernatants carefully removed, leaving aggregated bacteria settled on the bottom of the plate. The aggregates were photographed in a light microscope.

To determine the time course of bacterial agglutination, overnight cultures of P. aeruginosa PAO1 were washed in PBS and adjusted to an O.D. at 675 nm of 0.6. The bacteria were incubated in microcuvettes in a total volume of 500 μl. The concentrations of PSP peptides and added salts were varied and are indicated in the Figure legends. Samples were incubated at room temperature and the OD$_{675}$ recorded at regular intervals.

Bacterial Adhesion Assays—

Overnight cultures of P. aeruginosa PAO1 were diluted 1:100 in MHB and 100 μl of the bacterial suspension was mixed with 50 μg/ml of LL-37, GK-7, GL-13, KL-11 or lysozyme in PVC microtiter plates. The plates were incubated for 6 h at 32° C. under aerobic or reduced oxygen conditions. Bacterial growth was quantitated spectrophotometrically at 570 nm. Twenty-five μl of 1% crystal violet in dH$_2$O was added to each well and incubated 20 min at room temperature. The wells were emptied and washed three times in dH$_2$O and then incubated for 30 min with 200 μl of 95% ethanol. The OD at 570 nm was determined as a measure of biofilm formation. Growth and biofilm values were normalized against the mean of samples incubated with 0.01% acetic acid without peptides.

Gentamicin Protection Assay—

Overnight cultures of *P. aeruginosa* were diluted 1:5 in PBS and incubated for 1 h at room temperature with PSP peptides (100 μg/ml) or with an equivalent amount of 0.01% acetic acid. Aliquots (500 μl) of these samples were added to RAW 264.7 macrophage cells cultured in 24-well plates and incubated for 2 h at 37° C., 5% CO$_2$. The cells were washed in DMEM and then incubated with DMEM containing 200 μg/ml Gentamicin for 90 min at 37° C., 5% CO$_2$. The cells were again washed with DMEM and the incubated with 200 μl/well of PBS containing 1% Tween 20 for 5 min at room temperature. The cell extracts were diluted in LB and plated on LB agar plates. CFU were enumerated after overnight incubation at 37° C.

Statistics—

Data are expressed as mean±SEM. Treated and untreated samples were compared by unpaired Student's t-test, P<0.05 was considered statistically significant.

Results

Design of PSP Peptides.

For this study, the inventors used the peptides described in Example 1 above.

Antibacterial Activity.

We initially tested if the PSP peptides exhibit antibacterial activity, consistent with the predicted structural similarity of PSP and BPI and our preliminary data for intact PSP described above. Since GL-13 is more acidic than GK-7 or KL-11, the inventors initially used an amidated version of GL-13 (GL-13-NH2), which has a pI similar to that of the other PSP peptides (Table 1). To test if the PSP peptides inhibited bacterial growth, the minimal inhibitory concentration (MIC) of each peptide was determined in a standard broth dilution assay for *P. aeruginosa*, as described in Example 1 above. Briefly, two-fold serial peptide dilutions, starting at 84 μg/ml were performed for GK-7, GL-13-NH2, KL-11, LL-37 and lysozyme. LL-37 exhibited an MIC of 42 μg/ml against *P. aeruginosa* while lysozyme reduced growth of *P. aeruginosa* by about 50% at concentrations higher than 1 μg/ml but did not exhibit a defined MIC. None of the PSP peptides inhibited growth of *P. aeruginosa* in this assay. Similarly, none of the PSP peptides inhibited the growth of *A. actinomycetemcomitans* or *S. gordonii*.

As a second antibacterial assay, bactericidal activity was determined by incubating the peptides (10 or 100 μg/ml) with *P. aeruginosa, A. actinomycetemcomitans* or *S. gordonii* in 10 mM phosphate buffer. Surviving bacteria were enumerated on agar plates. The number of CFUs was highly variable between experiments and was never decreased by more than one order of magnitude (90%). In contrast, the control antimicrobial peptide LL-37 resulted in 100% killing of all three organisms at 10 or 100 μg/ml. Thus, the inventors concluded that the PSP peptides do not exhibit sufficient bactericidal activity to prevent bacterial growth in the overnight MIC assays.

Bacterial Agglutination.

The inventors noted that GL-13-NH2 caused matting of the bacteria in the 96-well plates used for MIC determinations, as opposed to a tight button of cells seen at the bottom of wells incubated with the other PSP peptides or control peptides. The matting was detected with all three bacterial species and was reminiscent of the passive hemagglutination described for sheep erythrocytes. To test if the peptide caused hemagglutination, unmodified sheep erythrocytes were incubated with each peptide in 96-well plates that were photographed to visualize the bacterial pellets. A tight button of cells was formed under most conditions, while GL13-NH2 caused passive hemagglutination.

Since the MIC plates were not incubated under identical conditions for all three bacterial species, we visualized agglutination of *P. aeruginosa, A. actinomycetemcomitans* and *S. gordonii* directly by incubating the bacteria with the PSP peptides in polystyrene plates. Agglutination was observed with all three bacterial species in the presence of GL-13-NH2, but not with the other PSP peptides or control antimicrobial peptides (FIG. 19). Aggregation was not seen in the absence of bacteria. These results suggest that GL-13-NH2 is an agglutinating peptide with activity against both Gram negative and Gram positive bacteria.

The kinetics of *P. aeruginosa* agglutination was examined spectrophotometrically by determining the decrease in turbidity of bacterial solutions with time in the presence of PSP-peptides. GL-13-NH2 caused essentially complete agglutination in 20 min at a concentration of 100 μg/ml and 50% agglutination at 50 μg/ml (FIG. 11A). The kinetics of agglutination were not significantly altered by the addition of 70 μM EDTA, 1 mM CaCl$_2$, 250 mM NaCl or 250 mM glucose, suggesting that divalent cations or the ionic strength did not affect agglutination (FIG. 11B).

The data in FIG. 11B show that bacterial agglutination by GL-13 is not affected by high salt concentrations or divalent cations. To determine if hydrophobic interactions could play a role in GL-13-mediated agglutination, *P. aeruginosa* were incubated with GL-13-NH2 in the presence or absence of 0.25% Tween 20 (this detergent concentration does not affect bacterial viability, not shown). FIG. 11C shows that GL-13 caused substantial agglutination as expressed by the decrease in optical density of a bacterial suspension. Tween 20 alone had no effect on bacterial agglutination while Tween-20 significantly limited the GL-13 induced agglutination. These data suggest that hydrophobic interactions play a role in the peptide-induced agglutination of *P. aeruginosa*.

Since GL-13-NH2 was the only amidated PSP peptide, the inventors tested if amidation played a role in agglutination of *P. aeruginosa*. The time course of agglutination for GL-13—NH2 was compared to that of the non-amidated peptide GL-13-OH (FIG. 12). The non-amidated peptide exhibited about 50% the agglutination ability of the amidated peptide. A further difference between GL-13 and the other peptides was the presence of an acidic amino acid in GL-13. The inventors modified this Asp residue to Asn to determine if an additional amino group would affect agglutination. FIG. 12 shows that a further small increase in agglutination was detected with this modification. Thus, an increase in the number of basic amine groups appears to increase the agglutination ability of GL-13.

Adhesion Assay.

To test if bacterial adhesion was affected by PSP peptides, *P. aeruginosa* was incubated in PVC microtiter plates and the adhered cells stained with crystal violet. FIG. 7A shows that GL-13-NH2 and KL-11 inhibited adhesion by 60% and 40%, respectively, with only a small (non-significant) reduction of bacterial growth. LL-37 showed strong reductions of both growth and adhesion while GK-7 and lysozyme affected neither growth nor adhesion under these conditions.

*P. aeruginosa* PAO1 adhesion (biofilm formation) is more pronounced under anaerobic than aerobic conditions. Thus, the effect of PSP peptides on adhesion was tested under reduced oxygen conditions. The cellular effect of reduced oxygen conditions was monitored by detecting the absence of pyocyanin production (not shown). Both GL-13-NH2 and KL-11 reduced biofilm formation under low oxygen conditions, (FIG. 7B).

The increased agglutination and decreased adhesion caused by GL-13 suggests that the peptide may affect bacterial clearance by macrophages and other phagocytic cells. To test this, P. aeruginosa was incubated with RAW 264.7 macrophage cells in the presence or absence of GL-13-NH2 or GK-7 and bacterial clearance was quantitated using a gentamicin protection assay. FIG. 13 shows that bacterial clearance increased 80% in the presence of GL-13-NH2, while the control peptide GK-7 had no effect on clearance.

Discussion

PSP is a potential host-defense protein found in saliva, oral epithelial cells and trachea. Intact PSP exhibits moderate antibacterial activity against P. aeruginosa. In this study, the inventors show that GL-13, a synthetic peptide derived from PSP, exhibits agglutinating activity, decreases infection in vivo and increases bacterial clearance by macrophages. The agglutinating activity of the GL-13 peptides was correlated with the predicted pI and charge of this peptide.

Based on the similarity of PSP and BPI, the inventors had predicted that the PSP peptides would exhibit bactericidal and bacteriostatic activities. Instead, the inventors discovered that GL-13 is an effective agglutinating peptide for different bacterial species, an activity that is not shared by the antimicrobial peptide LL-37. Indeed, peptide GL-13 effectively inhibited the spread of P. aeruginosa infection in Romaine lettuce leaves. Thus, in the presence of GL-13 infection was occasionally seen around the injection site but did not spread throughout the midrib of the leaves, as seen with control peptides. This is consistent with a role for agglutination in this infection model. While the inventors did find that GL-13 kills up to 90% of P. aeruginosa in 2 hours in low salt buffer, the effect was variable and did not extend to other bacterial species. In contrast, LL-37 effectively killed P. aeruginosa in vitro but had no effect in the lettuce model.

Agglutinating activity has not previously been reported for BPI or BPI-like proteins. Although the predicted structure and function of PSP were based on the structure of BPI, the present results suggest that the function of PSP may be more closely related to the salivary agglutinin DMBT1/gp340 and the lung surfactant proteins SP-A and SP-D than to BPI or the antimicrobial peptides LL-37 and defensins. The relative abundance of PSP in saliva is also consistent with a role in the physical interaction of bacterial cells. While PSP binds LPS, bacterial LPS is not required for agglutination since both Gram positive bacteria, which lack LPS, and unmodified erythrocytes were agglutinated by GL-13 peptides.

Saliva and the mucosal secretions of the upper airways contain a multitude of antibacterial proteins, including lactoferrin, lysozyme, LL-37, defensins, mucins, DMBT1/gp340, and histatins. Many of these proteins are cationic and it has been found that removal of cationic proteins (including PLUNC) from human airway fluid eliminates its inherent antibacterial activity. Consistent with this, the agglutination activity of GL-13 was directly correlated with the number of amine groups and predicted isoelectric point of the peptide.

Example 4

Inhibition of Inflammation

PSP was enriched from human saliva (IRB protocol 335.07) by ethanol-precipitation. The protein bound to immobilized P. aeruginosa LPS and was eluted with EDTA or Tween-20, suggesting that divalent cations and hydrophobic interactions played a role in binding. PSP is N-glycosylated. To test the role of N-glycosylation in LPS-binding, PSP was expressed in mammalian cells in the presence or absence of tunicamycin to obtain unglycosylated and glycosylated forms of PSP, respectively. Both forms of PSP bound to LPS, suggesting that N-glycosylation is not required for binding. To identify the LPS-binding domain, PSP peptides were designed based on the predicted structure of PSP. The peptide GL-13 inhibited binding of PSP to LPS suggesting that this peptide is derived from the binding domain (FIG. 20). To directly test if this peptide can inhibit LPS action, RAW264.7 macrophage cells were stimulated with P. aeruginosa LPS in the presence or absence of GL-13. The peptide inhibited LPS-induced TNFα secretion by about 90%, suggesting that the peptide has anti-inflammatory activity. The anti-inflammatory peptide polymyxin B only inhibited TNFα secretion by about 50% in this assay. The effect of GL-13 was not limited to P. aeruginosa LPS since the TNFα-stimulating activity of the LPS-analog, monophosphoryl lipid A, a vaccine adjuvant, was also inhibited by GL-13. Moreover, GL-13 inhibited the phorbol ester stimulated release of TNFα from RAW cells. GL-13 alone did not stimulate TNFα secretion or cause macrophage cell death, as judged from trypan blue exclusion. In summary, GL-13 is an effective inhibitor of the LPS-induced inflammatory response in macrophages and broadly inhibits this inflammatory response by affecting multiple signal transduction pathways.

Example 5

Cyanide Poisoning of C. elegans

GL-13 did not inhibit cyanide-mediated fast-killing of C. elegans (FIG. 14) or the production of pyocyanin in P. aeruginosa, suggesting that the peptide does not affect virulence factors in the bacteria. Preliminary results suggest that the peptide has low toxicity to macrophages, epithelial cells, C. elegans or mice (I.P. injection).

Example 6

LPS-Binding Activity of PSP

Parotid Secretory Protein (PSP) was enriched from human saliva (IRB protocol 335.07) by ethanol-precipitation. The protein bound to immobilized P. aeruginosa LPS and was eluted with EDTA or Tween-20, suggesting that divalent cations and hydrophobic interactions played a role in binding. PSP is N-glycosylated. To test the role of N-glycosylation in LPS-binding, PSP was expressed in mammalian cells in the presence or absence of tunicamycin to obtain unglycosylated and glycosylated forms of PSP, respectively. Both forms of PSP bound to LPS, suggesting that N-glycosylation is not required for binding. To identify the LPS-binding domain, the inventors designed PSP peptides based on the predicted structure of PSP. The peptide GL-13 inhibited binding of PSP to LPS suggesting that this peptide is derived from the binding domain (FIG. 20). To directly test if this peptide can inhibit LPS action, RAW264.7 macrophage cells were stimulated with P. aeruginosa LPS in the presence or absence of GL-13. The peptide inhibited LPS-induced TNFα secretion by about 90%, suggesting that the peptide has anti-inflammatory activity. The anti-inflammatory peptide polymyxin B only inhibited TNFα secretion by about 50% in this assay. The effect of GL-13 was not limited to P. aeruginosa LPS since the TNFα- stimulating activity of the LPS-analog, monophosphoryl lipid A, a vaccine adjuvant, was also inhibited by GL-13. Moreover, GL-13 inhibited the phorbol ester stimulated release of TNFα from RAW cells. GL-13 alone did not stimulate TNFα secretion or cause macrophage cell death, as judged from trypan blue exclusion (FIG. 21). Together these data show that GL-13 is an effective inhibitor of the LPS-induced inflammatory response in macrophages and that the peptide broadly inhibits this inflammatory response by affecting multiple signal transduction pathways.

Expression of hPSP:

Expression of hPSP in GH4C1 cells that were treated with or without 5 mM sodium butyrate. Secretion media and cell extracts were analyzed by immunoblotting using an antiserum to hPSP. The cells treated with sodium butyrate exhibited expression of hPSP. Different forms of PSP were expressed in butyrate treated GH4C1 cells and the secretion media analyzed by immunoblotting. The cells tested included cells expressing wild-type hPSP, cells transfected with a plasmid that contains the PSP cDNA insert in reverse orientation, and cells transfected with a plasmid coding for a mutant where Leu residues in the GL13 region were replaced by Ser residues. Only the wildtype cells expressed hPSP.

Affinity binding of hPSP:

Secretion medium from GH4C1 cells was loaded on LPS-Sepharose and the unbound fraction collected (this sample was divided on two lanes for PSP-WT). The column was washed and then eluted with PBS+EDTA. The eluted beads were boiled in SDS-sample buffer to release any remaining proteins. The results indicated that PSP binds LPS and is eluted with EDTA. PSP can also be eluted with Tween-20, suggesting hydrophobic interaction.

Assay to Determine if PSP is PSP is N-Glycosylated.

PSP-wild type (WT) or a reverse PSP insert (Rev) were expressed in GH4C 1 cells that were treated with or without tunicamycin, an inhibitor of N-glycosylation. Secretion medium was analyzed by immunoblotting using an antiserum to human PSP. Glycosylation accounted for about 7 kD in PSP.

LPS-Binding of Non-Glycosylated PSP.

PSP was produced in the absence or presence of tunicamycin. Secretion medium from GH4C1 Cells was reacted with LPS-Sepharose and the flow-through and Eluate fractions analyzed by immunoblotting for PSP. The flow-through fraction contained PSP and higher molecular weight contaminants, which reacted with the antibodies. Only PSP was detected in the eluate. The results indicated that N-glycosylation is not necessary for binding of PSP to LPS.

PSP Peptides Inhibit LPS Activity.

PSP peptides inhibit LPS-induced TNFα secretion from RAW 264.7 macrophage cells (FIGS. 15A and 15B). GL-13 strongly inhibits the LPS-stimulated secretion of TNFα.

PSP Peptides Inhibit MPLA-Induced TNFα Secretion from RAW 264.7 Macrophage Cells.

The vaccine adjuvant monophosphoryl lipid A (MPLA) a low-toxicity derivative of LPS was used to stimulate RAW cells in the presence or absence of PSP peptides (200 μg/ml) or the anti-inflammatory peptide polymyxin B (PMX). Control samples were incubated with the peptides alone. PMX, but not PSP peptides, exhibited toxicity to RAW cells, as evidenced by increased TNFα release as quantitated by ELISA (FIG. 16). Thus, GL-13 inhibits the activity of the LPS derivative MPLA.

PSP Peptides Inhibit TNFα Secretion from RAW 264.7 Macrophage Cells.

RAW cells were stimulated with 100 nM Phorbol 12,13 didecanoate (+) or the inactive 4α-PDD (−) in the presence or absence of PSP peptides (200 μg/ml) or the anti-inflammatory peptide polymyxin B (PMX) (FIG. 17A). GL-13 strongly inhibits the phorbol ester-stimulated secretion of TNFα. FIG. 17B shows the effect of GL-13 was not a direct inhibition of the TNFα ELISA, since the ELISA standard curve was not affect by the presence of GL-13 or GK-7.

RAW Cell Viability. Cell Death Assay.

RAW 264.7 cells were incubated with 200 μg/ml of PSP peptides for 24 h. At the end of the incubation period the cells were stained with trypan blue and photographed in the light microscope. No significant cell death was detected with any of the peptides (FIG. 21).

GL-13 Protects Mice in an LPS Sepsis Model.

C57BL/6 mice were sensitized with D-galactosamine and injected with 100 ng/mouse (50 μg/kg) of P. aeruginosa LPS that had been preincubated for 1 h RT with or without 100 μg/mouse of GL-13 (FIG. 18). Controls received LPS and 0.9% saline. The mice were observed at the times indicated and % survival calculated. The results are from two independent experiments. After 12 hours, survival in the LPS+GL-13 group was significantly different from the LPS group, P<0.04 (N=10). GL-13 protects mice from LPS-induced sepsis.

GL-13 Enhances the Clearance of P. aAeruginosa by Macrophages (Phagocytosis).

FIG. 13 shows that GL13 enhanced the phagocytosis of P. aeruginosa.

Peptides do not Cause Hemagglutination in Circulation.

GL-13 did not cause cell death in mouse macrophage cultures (RAW 264.7 cells; FIG. 21) and did not cause lethality when injected intra-peritoneally in C57BL/6 mice (FIG. 18). Since some antimicrobial peptides are known to be hemotoxic, the inventors tested if GL-13 caused hemagglutination or hemolysis of sheep red blood cells. In PBS buffer, the three GL-13 peptides GL-13-NH2, GL-13-OH and GL-13-D/N—NH2 caused hemagglutination in the absence of 5% serum. Other PSP peptides (GK7, KL11), polymyxin B (PMX) or LL-37 did not cause hemagglutination. (FIG. 22). Hemagglutination was not seen in the presence of 5% serum, suggesting that the peptides would not cause hemagglutination in circulation.

GL-13 Peptides do not Cause Hemolysis Under In Vivo Conditions.

To test if GL-13 caused hemolysis, sheep red blood cells were incubated with three different GL-13 peptides and control peptides in PBS. Hemolysis, as expressed by hemoglobin release, was determined spectrophotometrically. GL-13-D/N—NH2 showed hemolysis in serum-free PBS (FIG. 23A). The effect was about 50% of the maximal hemolysis observed when sheep red blood cells were incubated in distilled water. As in the case of hemagglutination, the addition of 5% serum prevented peptide-induced hemolysis (FIG. 23B). These results suggest that the GL-13 peptides would not cause hemolysis under in vivo conditions.

Conclusions

The salivary protein Parotid Secretory Protein binds LPS. N-glycosylation of PSP is not necessary for LPS binding. Based on the structure of the LPs-binding protein BPI, potential anti-inflammatory peptides were identified in the PSP sequence. The PSP peptide GL-13 inhibits the stimulation of macrophages by LPS, MPLA and phorbol ester. Unlike polymyxin B, GL-13 is not cytotoxic to macrophages. GL-13 has a protective effect in an LPS-induced in vivo sepsis model, as it protected mice from sepsis. GL-13 decreases infection, and increases phagocytosis of bacteria. GL-13 does not inhibit cyanide poisoning.

Example 7

Peptide Mimetics

Various experimental techniques yield peptides that are biologically active but have unfavourable pharmacological properties, such as difficulty to produce in large quantities, and sensitive to protease digestion. Because peptides are often poor drug candidates, the need arises for bioequivalent compounds with better pharmacological properties. These peptide mimics are inexpensive nonpeptidic oligomers and polymers that adopt amphiphilic secondary structures and exhibit potent and selective targeted activity. Starting from a known spatial structure of a natural peptide template, the aim is to find compounds that mimic the function of a peptide but have improved cellular transport properties, low toxicity, few side effects and more rigid structures as well as protease resistance. These functionally and structurally similar organic compounds are called peptide mimetics. Peptide mimetics may have several potential advantages over native peptides, such as increased stability, increased lipophilicity, increased rigidity, decreased size, and affordability of production.

Various methods exist for developing peptide mimetics. These include computational as well as experimental screening methods. One method is to identify small peptides that are essential for the interactions of the protein. Subsequently, mimetics for these peptides are designed that can be used as drugs. On the basis of a known protein structure, scaffolding templates for binders can also be constructed and then optimized using different methods. Peptide mimetics for PSP peptides encompass amphiphilic cationic molecules, e.g., substituted arylamides. Candidate molecules are screened using the antimicrobial assays described for the PSP peptides.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms “a” and “an” and “the” and similar referents in the context of describing the invention are to be construed to cover both the singular and the plural, unless otherwise indicated herein or clearly contradicted by context. The terms “comprising,” “having,” “including,” and “containing” are to be construed as open-ended terms (i.e., meaning “including, but not limited to”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated and purified Parotid Secretory Protein (PSP) peptide of 13 to 50 amino acids in length comprising the amino acid sequence of SEQ ID NO: 8, SEQ ID NO: 11, SEQ ID NO: 12, or SEQ ID NO: 13.

2. The isolated and purified Parotid Secretory Protein (PSP) peptide of claim 1, wherein the peptide is amidated at its C-terminal end.

3. The PSP peptide of claim 1, wherein the peptide is between 13 and 20 amino acids in length.

4. The PSP peptide of claim 1, wherein the peptide is between 13 and 15 amino acids in length.

5. The PSP peptide of claim 1, wherein the peptide is 13 amino acids in length.

6. The PSP peptide of claim 1, wherein the peptide is linear.

* * * * *

UNITED STATES PATENT AND TRADEMARK OFFICE
CERTIFICATE OF CORRECTION

PATENT NO.       : 8,569,449 B2                                    Page 1 of 1
APPLICATION NO. : 12/599021
DATED            : October 29, 2013
INVENTOR(S)      : Sven-Ulrik Gorr It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gln Ile Ile Asn Leu Lys
  1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Gln Glu Ala Glu Lys Leu Leu Asn Asn
```

```
              1               5                  10
```

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Lys Leu Leu Asn Asn Val Ile Ser Lys Leu Leu
 1               5                  10
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Lys Leu Leu Asn Asn Val Ile Ser Lys
 1               5
```

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Gln Ile Ile Asn Leu Lys Ala Ser Leu Asp Leu Leu
 1               5                  10
```

<210> SEQ ID NO 6
<211> LENGTH: 249
<212> TYPE: PRT
<213> ORGANISM: Homo sapiens

<400> SEQUENCE: 6

```
Met Leu Gln Leu Trp Lys Leu Val Leu Leu Cys Gly Val Leu Thr Gly
 1               5                  10                  15

Thr Ser Glu Ser Leu Leu Asp Asn Leu Gly Asn Asp Leu Ser Asn Val
                 20                  25                  30

Val Asp Lys Leu Glu Pro Val Leu His Glu Gly Leu Glu Thr Val Asp
             35                  40                  45

Asn Thr Leu Lys Gly Ile Leu Glu Lys Lys Val Asp Leu Gly Val
         50                  55                  60

Leu Gln Lys Ser Ser Ala Trp Gln Leu Ala Lys Gln Lys Ala Gln Glu
65                  70                  75                  80

Ala Glu Lys Leu Leu Asn Asn Val Ile Ser Lys Leu Leu Pro Thr Asn
                 85                  90                  95

Thr Asp Ile Phe Gly Leu Lys Ile Ser Asn Ser Leu Ile Leu Asp Val
                100                 105                 110

Lys Ala Glu Pro Ile Asp Gly Lys Gly Leu Asn Leu Ser Phe Pro
             115                 120                 125

Val Thr Ala Asn Val Thr Val Ala Gly Pro Ile Ile Gly Gln Ile Ile
         130                 135                 140

Asn Leu Lys Ala Ser Leu Asp Leu Leu Thr Ala Val Thr Ile Glu Thr
```

-continued

```
                145                 150                 155                 160
Asp Pro Gln Thr His Gln Pro Val Ala Val Leu Gly Glu Cys Ala Ser
                165                 170                 175

Asp Pro Thr Ser Ile Ser Leu Ser Leu Leu Asp Lys His Ser Gln Ile
                180                 185                 190

Ile Asn Lys Phe Val Asn Ser Val Ile Asn Thr Leu Lys Ser Thr Val
                195                 200                 205

Ser Ser Leu Leu Gln Lys Glu Ile Cys Pro Leu Ile Arg Ile Phe Ile
        210                 215                 220

His Ser Leu Asp Val Asn Val Ile Gln Gln Val Val Asp Asn Pro Gln
225                 230                 235                 240

His Lys Thr Gln Leu Gln Thr Leu Ile
                245

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Leu-(CONH2)

<400> SEQUENCE: 7

Gly Gln Ile Ile Asn Leu Lys Ala Ser Leu Asp Leu Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Leu-(CONH2)

<400> SEQUENCE: 8

Gly Gln Ile Ile Asn Leu Lys Ala Ser Leu Asn Leu Leu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Leu-(COOH)

<400> SEQUENCE: 9

Gly Gln Ile Ile Asn Leu Lys Ala Ser Leu Asn Leu Leu
1               5                   10

<210> SEQ ID NO 10
<211> LENGTH: 37
<212> TYPE: PRT
<213> ORGANISM: Homo sapiens
```

```
<400> SEQUENCE: 10

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gln Ile Ile Asn Leu Lys Ala Ser Leu Gln Leu Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gln Ile Ile Asn Leu Lys Ala Ser Leu Lys Leu Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gln Ile Ile Asn Leu Lys Ala Ser Leu Arg Leu Leu
1               5                   10
```